(12) United States Patent
Miyamoto et al.

(10) Patent No.: US 8,523,762 B2
(45) Date of Patent: Sep. 3, 2013

(54) ENDOSCOPE SYSTEM, ENDOSCOPE, SUPPORTING MEMBER, AND METHOD OF USING ENDOSCOPE SYSTEM

(75) Inventors: Satoshi Miyamoto, Hachioji (JP); Kousuke Motai, Hachioji (JP); Yasuhito Kura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1489 days.

(21) Appl. No.: 12/114,235

(22) Filed: May 2, 2008

(65) Prior Publication Data

US 2008/0269559 A1    Oct. 30, 2008

Related U.S. Application Data

(63) Continuation of application No. PCT/JP2005/020303, filed on Nov. 4, 2005.

(51) Int. Cl.
  *A61B 1/04* (2006.01)
(52) U.S. Cl.
  USPC ........... 600/116; 600/114; 600/115; 600/170; 600/171
(58) Field of Classification Search
  USPC .................................. 600/115–116, 170–171
  See application file for complete search history.

(56) References Cited

U.S. PATENT DOCUMENTS

| | | | |
|---|---|---|---|
| 4,040,413 A | | 8/1977 | Ohshiro |
| 4,066,070 A * | | 1/1978 | Utsugi ........................... 600/116 |
| 4,148,307 A * | | 4/1979 | Utsugi ........................... 600/116 |
| 4,224,929 A * | | 9/1980 | Furihata ........................ 600/116 |
| 4,875,897 A | | 10/1989 | Lee |
| 4,941,457 A * | | 7/1990 | Hasegawa ...................... 600/142 |
| 4,983,165 A * | | 1/1991 | Loiterman ................... 604/95.03 |
| 5,090,259 A | | 2/1992 | Shishido et al. |
| 5,658,311 A * | | 8/1997 | Baden ........................... 606/192 |
| 5,830,222 A | | 11/1998 | Makower |
| 6,007,482 A * | | 12/1999 | Madni et al. .................. 600/115 |
| 7,963,911 B2 * | | 6/2011 | Turliuc ......................... 600/115 |
| 8,038,598 B2 * | | 10/2011 | Khachi ........................ 600/116 |

(Continued)

FOREIGN PATENT DOCUMENTS

| | | |
|---|---|---|
| EP | 1 441 215 A1 | 7/2004 |
| EP | 1 654 976 A2 | 5/2006 |

(Continued)

OTHER PUBLICATIONS

Extended Supplementary European Search Report dated Feb. 4, 2013 in European Patent Application No. 05805409.9.

*Primary Examiner* — Matthew J Kasztejna
(74) *Attorney, Agent, or Firm* — Scully, Scott, Murphy & Presser, P.C.

(57) ABSTRACT

An endoscope system includes: an endoscope including an elongated insertion portion provided with a bendable bending portion, the insertion portion being inserted into a duodenum; and a first balloon to a fourth balloon for moving a one-side surface of a distal end portion located nearer to a distal end side than the bending portion in the insertion portion in parallel with respect to a field of view direction S of an objective lens which is a diameter direction of the insertion portion, separately from bending of the bending portion, the one-side surface being located in a circumferential direction along an insertion direction W of the insertion portion and parallel to a central axis P of the insertion portion.

4 Claims, 29 Drawing Sheets

(56) References Cited

U.S. PATENT DOCUMENTS

| | | | |
|---|---|---|---|
| 8,187,173 B2* | 5/2012 | Miyoshi | 600/115 |
| 2002/0058858 A1 | 5/2002 | Ogura et al. | |
| 2002/0143237 A1* | 10/2002 | Oneda et al. | 600/116 |
| 2004/0181148 A1 | 9/2004 | Uchiyama et al. | |
| 2010/0056865 A1* | 3/2010 | Nagamachi et al. | 600/116 |

FOREIGN PATENT DOCUMENTS

| | | |
|---|---|---|
| JP | 58-502037 | 12/1983 |
| JP | Sho 62-22623 | 1/1987 |
| JP | 1-214739 | 8/1989 |
| JP | 1-214739 A | 8/1989 |
| JP | 03-222930 | 10/1991 |
| JP | 05-003851 | 1/1993 |
| JP | 2000-342528 | 12/2000 |
| JP | 2002-514111 | 5/2002 |
| JP | 2002-177202 | 6/2002 |
| JP | 2004-097391 | 4/2004 |
| JP | 2004-121749 | 4/2004 |
| JP | 2005-270335 | 10/2005 |
| WO | WO 83/01893 | 6/1983 |
| WO | WO 97/13463 | 4/1997 |
| WO | WO 98/46119 | 10/1998 |
| WO | WO 03/038410 A1 | 5/2003 |

* cited by examiner

K=D

K=D

K≠D

ENDOSCOPE SYSTEM, ENDOSCOPE, SUPPORTING MEMBER, AND METHOD OF USING ENDOSCOPE SYSTEM

CROSS REFERENCE TO RELATED APPLICATION

This application is a continuation application of PCT/JP2005/020303 filed on Nov. 4, 2005, the entire contents of which are incorporated herein by this reference.

BACKGROUND OF THE INVENTION

1. Field of the Invention

The present invention relates to an endoscope system, an endoscope, and a supporting member that are provided with a moving mechanism for moving in a lumen an endoscope insertion portion inserted in the lumen, and a method of using the endoscope system.

2. Description of the Related Art

In recent years, there has been performed so-called ERCP (Endoscopic Retrograde Cholangiopancreatography), in which a region to be inspected in a canaliculus in a body cavity, i.e., in a lumen, that is, the region to be inspected in a pancreaticobiliary duct system for example is inspected and treated using a side-view endoscope including an image pickup optical system disposed on a side surface of a distal end of an insertion portion.

The ERCP using the side-view endoscope (hereinafter called simply as endoscope) includes, in addition to an inspection such as cholangiography and pancreatography by a treatment instrument like a catheter, a therapeutic treatment by collecting gallstones in the common bile duct or the like with the treatment instrument such as a balloon or a basket.

In addition, in performing the ERCP, a technique is required for insertion of a treatment instrument such as catheter (hereinafter called simply as treatment instrument) into the bile duct or the pancreatic duct, since the pancreatic duct and the bile duct are very narrow ducts.

Therefore, normally in inserting a treatment instrument into the bile duct or the pancreatic duct, a distal end of an endoscope insertion portion is first inserted to near the duodenum papilla, and therefrom, under the observation of the endoscope, field of view of an endoscope is ensured by adjusting a distance between the papilla and the distal end of the endoscope insertion portion by advancing/retreating operation, bending operation, or the like of the endoscope itself.

After that, by pushing-in operation of the treatment instrument from a proximal end side of a treatment instrument insertion conduit provided inside of the insertion portion, the treatment instrument is projected from an aperture portion of the treatment instrument insertion conduit formed on a side surface of the distal end of the insertion portion and the projected treatment instrument is inserted into the bile duct and the pancreatic duct through the papilla.

Note that in inserting the treatment instrument into the bile duct or the pancreatic duct from a distal end aperture portion of the treatment instrument insertion conduit, it is well-known that an insertion angle can be fine-tuned by using a so-called treatment instrument raising table (hereinafter called simply as raising table) which is provided in the vicinity of the distal end aperture portion.

Incidentally, as described above, the pancreatic duct and the bile duct are very narrow ducts. Therefore, when insertion of the treatment instrument into the bile duct or the pancreatic duct by push-in operation is difficult even with the use of the raising table, it is necessary to perform advancing/retreating operation, bending operation, or the like of the endoscope itself again so as to bring the endoscope close to the papilla.

However, if the advancing/retreating operation, bending operation or the like of the endoscope itself is performed again, the field of view direction is changed. Therefore, it is necessary to perform adjustment to secure the field of view of the endoscope again. In addition, particularly, if bending operation is performed in left/right direction with respect to the papilla, the projecting direction of the treatment instrument projecting from the distal end aperture portion and the direction of the bile duct, for example, are deviated from each other to left and right, thereby causing a difficulty in insertion of the treatment instrument. As a result, an operator needs to adjust the projecting direction of the treatment instrument and the direction of the bile duct again, which is a cumbersome work for the operator.

Note that, in the side-view endoscope, the raising table adjusts the treatment instrument in up/down direction with respect to the papilla after securing the field of view, so that the raising table cannot coincide the projecting direction of the treatment instrument and the direction of the bile duct which are deviated from each other to left and right.

In addition, in a case of insertion of the treatment instrument using the raising table, a tendency to bending is given to the treatment instrument from the raising table, as the treatment instrument undergoes several cases. As a result, there is a problem that insertion of the treatment instrument into the bile duct or the pancreatic duct by push-in operation becomes difficult due to the tendency to bending.

In view of such a problem, in a moving mechanism disclosed in Japanese Unexamined Patent Application Publication No. 2004-97391, for example, three balloons contactable with inside of the lumen are provided on an outer circumference of a distal end portion which is located on a side nearer to the distal end side than a bending portion in the endoscope insertion portion and each of the balloons is inflated and contracted in a state where three balloons are inflated to contact inside of the body cavity, thereby enabling a distal end side of an endoscope insertion portion to move in a lumen in parallel with respect to a field of view direction of the endoscope while securing the field of view of the endoscope, without the advancing/retreating operation, bending operation or the like of the endoscope itself after securing the field of view of the endoscope.

Note that the moving mechanism in the present publication is applied to a direct-view endoscope in the publication. However, if the moving mechanism is applied to a side-view endoscope, it is possible, after securing a field of view of an endoscope, to bring a distal end portion of the endoscope close to a region to be inspected in a lumen while securing the field of view of the endoscope, thereby facilitating the insertion of the treatment instrument into the bile duct or the pancreatic duct.

Furthermore, Japanese Unexamined Patent Application Publication No. 2000-342528 discloses a technique to facilitate the insertion of the treatment instrument into the bile duct or the pancreatic duct. In the technique, on an outer circumference of a distal end portion, on which a treatment instrument insertion conduit is open, located on the side nearer to the distal end than the bending portion of the insertion portion of the side-view endoscope, a circumferential balloon covering the outer circumference is provided, and after the field of view of the endoscope is secured, the circumferential balloon is inflated to contact the inside of the body cavity and enables the distal end portion of the endoscope to be fixed in the body cavity.

SUMMARY OF THE INVENTION

In brief, an endoscope system of the present invention includes: an endoscope including an elongated insertion portion provided with a bendable bending portion, the insertion portion being inserted into a lumen; and a moving mechanism for moving a one-side surface located nearer to a distal end side than the bending portion of the insertion portion in parallel in a diameter direction of the insertion portion, separately from bending of the bending portion, the one-side surface being located in a circumferential direction along an insertion direction of the insertion portion.

Furthermore, an endoscope of the present invention includes an elongated insertion portion provided with a bendable bending portion, the insertion portion being inserted in a lumen, and the endoscope comprises a flexible tube portion having flexibility provided in a linked manner between the bending portion of the insertion portion and an operation portion; and a moving mechanism disposed on a distal end portion of the flexible tube portion, the moving mechanism moving a one-side surface located nearer to a distal end side than the bending portion of the insertion portion in parallel in a diameter direction of the insertion portion, separately from bending of the bending portion, the one-side surface being located in a circumferential direction along an insertion direction of the insertion portion and being parallel to a central axis of the insertion portion.

Moreover, supporting members of the present invention are disposed in a circumferential direction of an insertion portion of an endoscope so as to oppose to each other at line-symmetric positions with respect to one of either a first axis passing a central axis of the endoscope and parallel to a field of view direction of an objective lens or a second axis passing the central axis and orthogonal to the first axis, one of the supporting members expanding in a diameter direction of the endoscope and the other of the supporting members contracting in the diameter direction interlockingly with the expansion.

A method of using an endoscope system of the present invention comprises: a procedure in which an elongated insertion portion provided with a bending portion is inserted into a lumen; a procedure in which a field of view with respect to a region to be inspected is secured by an objective lens by bending the bending portion, the objective lens being provided on a one-side surface located nearer to a distal end side than the bending portion of the insertion portion, the one-side surface being located in a circumferential direction along an insertion direction of the insertion portion and being parallel to a central axis of the insertion portion; a procedure in which bending of the bending portion is fixed; a procedure in which a treatment instrument is projected from an aperture provided on the one-side surface; a procedure in which the one-side surface is moved in parallel by a moving mechanism in a diameter direction of the insertion portion separately from the bending of the bending portion, and a distal end of the treatment instrument is brought close to the region to be inspected; and a procedure in which the treatment instrument is inserted into the region to be inspected.

The above and other objects, features and advantages of the invention will become more clearly understood from the following description referring to the accompanying drawings.

BRIEF DESCRIPTION OF THE DRAWINGS

FIG. 36 is a cross-sectional view showing a state where a distal-side switch of FIG. 35 is turned on.

FIG. 37 is a cross-sectional view showing a state where the distal-side switch and a proximal-side switch of FIG. 35 are turned on.

DETAILED DESCRIPTION OF THE PREFERRED EMBODIMENT(S)

Hereinafter, embodiments of the present invention will be described with reference to the drawings. Note that an endoscope will be described taking a side-view medical endoscope as an example.

(First Embodiment)

Figure 1:
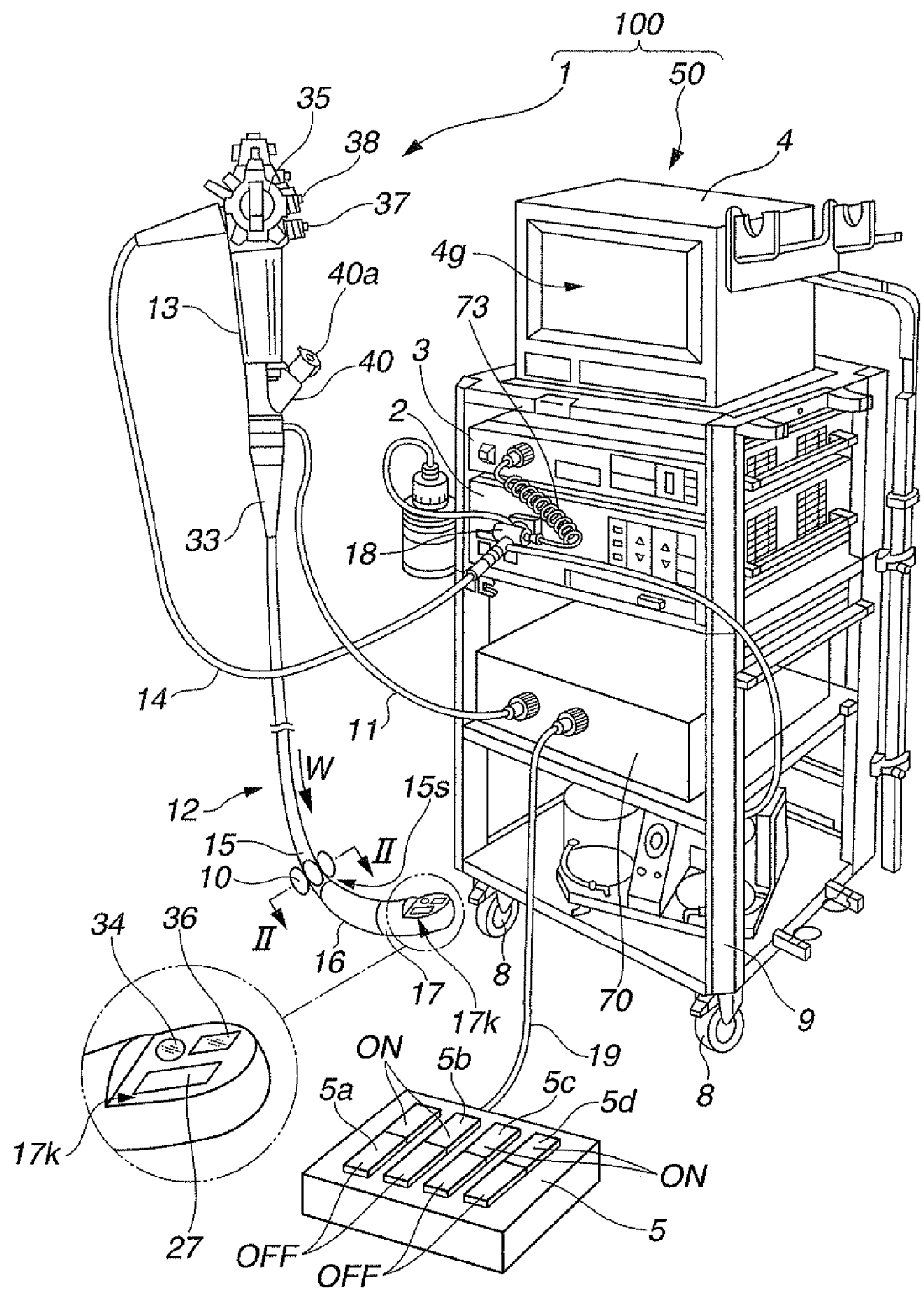
FIG. 1 is an appearance perspective view of an endoscope system showing a first embodiment of the present invention, seen from diagonally forward upper right.
Figure 2:
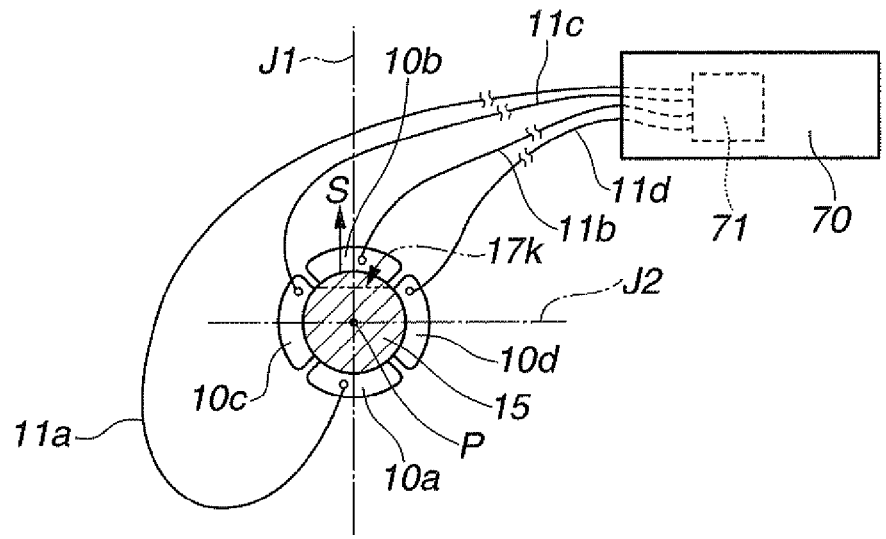
FIG. 2 is a pattern diagram showing a cross section of a flexible tube portion of an endoscope along the II-II line in FIG. 1, together with balloon conduits and a balloon control unit.
Figure 3:
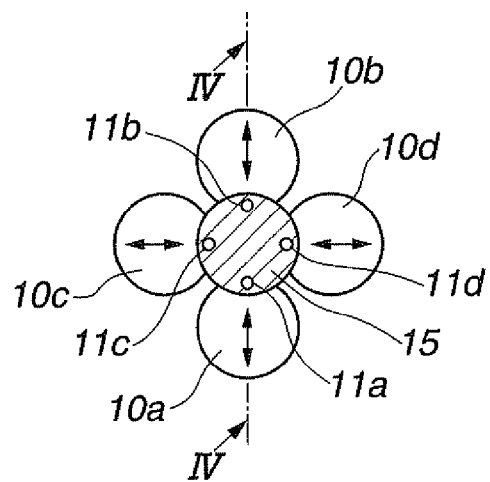
FIG. 3 is a cross-sectional view of the flexible tube portion showing the balloon conduits disposed inside of an insertion portion of FIG. 1, together with inflated balloons.
Figure 4:
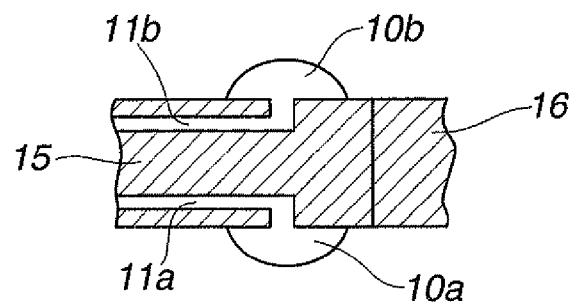
FIG. 4 is a cross-sectional view along the IV-IV line of FIG. 3.

FIG. 1 is an appearance perspective view of an endoscope system showing a first embodiment of the present invention, seen from diagonally forward upper right, FIG. 2 is a pattern diagram showing a cross section of a flexible tube portion of an endoscope along the II-II line in FIG. 1, together with balloon conduits and a balloon control unit, FIG. 3 is a cross-sectional view of the flexible tube portion showing the balloon conduits disposed inside of an insertion portion of FIG. 1, together with inflated balloons, and FIG. 4 is a cross-sectional view along the IV-IV line of FIG. 3. Note that, in FIGS. 2 to 4, an internal configuration of a flexible tube portion is shown by omitting the components except balloon conduits.

As shown in FIG. 1, an endoscope system 100 includes a side-view endoscope 1 including balloons 10 as supporting members, and a peripheral device 50.

The endoscope 1 includes a main portion configured of an operation portion 13, an insertion portion 12 provided in a linked manner on a distal end side of an insertion direction of the operation portion 13, and a universal cord 14 connecting the endoscope 1 and the peripheral device 50. At a position connecting the insertion portion 12 and the operation portion 13 is provided an insertion portion protecting member 33 for protecting the insertion portion 12.

The peripheral device 50 includes a main portion configured of a light source device 2, a video processor 3, a connection cable 73 electrically connecting the light source device 2 and the video processor 3, a monitor 4 having a monitor screen 4g, a balloon control unit 70, all of which are disposed on a rack 9 with castors 8 attached at lower parts thereof, and a foot switch 5 connected to the balloon control unit 70 with a cable 19.

A connector 18 disposed at a distal end of the universal cord 14 extended from the operation portion 13 of the endoscope 1 is connected to the light source device 2 of the peripheral device 50. The connector 18 includes a base not shown configuring an end portion of a fluid conduit, a light guide base and an electric contact portion, also not shown, configuring an end portion of a light guide.

The light guide is guided from the universal cord 14, via insides of the operation portion 13 and the insertion portion 12 of the endoscope 1, to a distal end portion 17, to be described later, of the insertion portion 12, and transmits illumination light from the light source device 2 to an illumination lens 36 of the distal end portion 17 to be described later, to diffusely irradiate the illumination light into a body cavity.

The operation portion 13 of the endoscope 1 includes: a bending operation knob 35; an air/water feeding operation button 37; a suction operation button 38; a treatment instrument insertion port 40 having an aperture 40a to insert a treatment instrument 60 such as a catheter (see FIG. 8) into a treatment instrument insertion channel not shown disposed inside of the insertion portion 12 of the endoscope 1; and a balloon insertion port not shown to insert a balloon conduit 11 extended from the balloon control unit 70 into inside of the endoscope 1.

The insertion portion 12 of the endoscope 1 is configured of the distal end portion 17, a bending portion 16, and a flexible tube portion 15 having flexibility. The bending portion 16 is operated to be bent, for example, in four directions by a bending operation knob 35 provided to the operation portion 13, and disposed between the distal end portion 17 and the flexible tube portion 15.

On one side of a circumferential direction along an insertion direction W of the insertion portion 12, that is, on one side of an outer circumferential surface of the insertion portion 12, a one-side surface 17k which is generally parallel to the insertion direction is formed by notching the one side. On the one-side surface 17k is provided a channel aperture portion 27 serving as an aperture of the distal end portion of the above-described treatment instrument insertion channel.

Note that a treatment instrument raising table not shown for raising a treatment instrument 60 is disposed inside of the channel aperture portion 27 so as to be located in the vicinity of the aperture. The treatment instrument raising table changes an advancing direction of the treatment instrument 60 inserted in the treatment instrument insertion channel, from an advancing direction in the treatment instrument insertion channel to a direction of the channel aperture portion 27, and also fixes a position of the treatment instrument 60 by raising the treatment instrument 60 to the maximum.

In addition, in the vicinity of the channel aperture portion 27 on the one-side surface 17k are provided the objective lens 34 of an image pickup unit, not shown, and an illumination lens 36 of the illumination optical system which are incorporated in the distal end portion 17.

On an outer circumferential surface of a distal end portion 15s of the flexible tube portion 15 of the endoscope 1, along the circumferential direction of the outer circumferential surface, four balloons 10, which are inflatable/contractable by air feeding and sucking, for example, are disposed integrally with the flexible tube portion 15, as shown in FIGS. 2, 3.

In detail, as shown in FIG. 2, the balloons 10 include, on the outer circumferential surface of the distal end portion 15s of the flexible tube portion 15, a third balloon 10c and a fourth balloon 10d disposed so as to oppose to each other at line-symmetric positions with respect to a first axis J1 which passes a central axis P of the endoscope parallel to the one-side surface 17k and is parallel to a field of view direction S of the objective lens 34, and a first balloon 10a and a second balloon 10b disposed so as to oppose to each other at line-symmetric positions with respect to a second axis J2 which passes the central axis P and is orthogonal to the first axis J1.

More specifically, the second balloon 10b is disposed on the outer circumferential surface of the distal end portion 15s of the flexible tube portion 15 so as to be located at the position on the first axis J1, which is on the side of the field of view direction S of the objective lens 34, in other words, on the side where the one-side surface 17k is formed. The first balloon 10a is disposed at the position on the first axis J1, which is on an opposite direction side of the field of view direction S of the objective lens 34.

Note that, in the present embodiment, the objective lens 34 is located on the side close to a papilla 95 when the endoscope 1 is inserted into a body cavity and the objective lens 34 observes the papilla 95 as a region to be inspected, that is, the duodenum 90, so that the second balloon 10b is located on the side close to the papilla 95 and the first balloon 10a is located on the side away from the papilla 95.

In addition, the third balloon 10c is disposed at the position on the second axis J2, which is on one end side of the direction orthogonal to the field of view direction S of the objective lens 34, and the fourth balloon 10d is disposed at the position on the second axis, which is on the other end side of the direction orthogonal to the field of view direction S of the objective lens 34.

Note that, in the present embodiment, it is assumed that the third balloon 10c is located on the left side with respect to the papilla 95 when the endoscope 1 is inserted into the body cavity, that is, the duodenum 90 and the fourth balloon 10d is located on the right side with respect to the papilla 95.

As shown in FIG. 2, four balloon conduits 11a to 11d configuring the balloon conduit 11 extended from the balloon control unit 70 are communicated with the balloons 10a to 10d, respectively.

As shown in FIG. 2, each of the balloon conduits 11a to 11d is extended from an air feeding/sucking device 71 as an air feeding/sucking mechanism configuring an expansion/contraction mechanism disposed in the balloon control unit 70, to be inserted into the operation portion 13 and the insertion portion 12 from a balloon insertion port formed on the operation portion 13 of the endoscope 1, and are connected to be in communication with the balloons 10a to 10d, respectively, as shown in FIGS. 3, 4. Note that also each of the balloon conduits 11a to 11d configures the expansion/contraction mechanism in the present invention.

The balloons 10a to 10d will be described in detail in an explanation of working thereof later. After the endoscope 1 is inserted into a body cavity and the balloons 10a to 10d are inflated to contact inside of the body cavity, the balloons are further inflated or contracted, to move, separately from the bending operation of the bending portion 16, the one-side surface 17k of the distal end portion 17 located nearer to the distal end side than the bending portion 16 in the insertion portion 12, in parallel to the field of view direction S of the objective lens 34 which is a diameter direction of the insertion portion 12. The balloons 10a to 10d configure a moving mechanism of the present invention.

The air feeding/sucking device 71 is configured of a pump and the like, for example, and inflates and contracts each of the balloons 10a to 10d by sending and sucking air to and from each of the balloons 10a to 10d.

The air feeding/sucking device 71 sends air to the first balloon 10a via the balloon conduit 11a to inflate the first balloon 10a by pressurization while an on-button of a distal-side switch 5a disposed on the foot switch 5 is depressed, and sucks air from the first balloon 10a via the balloon conduit 11a to contract the first balloon 10a by depressurization while an off-button is depressed.

Furthermore, the air feeding/sucking device 71 sends air to the second balloon 10b via the balloon conduit 11b to inflate the second balloon 10a by pressurization while an on-button is depressed from the proximal-side switch 5b, and sucks air from the second balloon 10b via the balloon conduit 11b to contract the second balloon 10b by depressurization while an off-button is depressed.

The air feeding/sucking device 71 sends air to the third balloon 10c via the balloon conduit 11c to inflate the third balloon 10c by pressurization while an on-button is depressed from the left-side switch 5c, and sucks air from the third balloon 10c via the balloon conduit 11c to contract the third balloon 10c by depressurization while an off-button is depressed.

Furthermore, the air feeding/sucking device 71 sends air to the fourth balloon 10d via the balloon conduit 11d to inflate the fourth balloon 10d by pressurization while an on-button is depressed from the right-side switch 5d, and sucks air from the fourth balloon 10d via the balloon conduit 11d to contract the fourth balloon 10d by depressurization while an off-button is depressed.

Next, working of the endoscope system 100 thus configured is described with reference to the above-described FIGS. 1 to 4, and FIGS. 5 to 22.

Note that, in the explanation of the working below, description will be made with reference to FIGS. 5 to 14 on a case where the endoscope insertion portion 12 is inserted into the duodenum 90, and then the one-side surface 17k of the distal end portion 17 of the endoscope insertion portion 12 is brought close to the papilla 95 to insert a catheter as the treatment instrument into the bile duct as a region to be inspected via the papilla. Therefore, the catheter is attached with a reference numeral 60 hereinafter.

Figure 5:
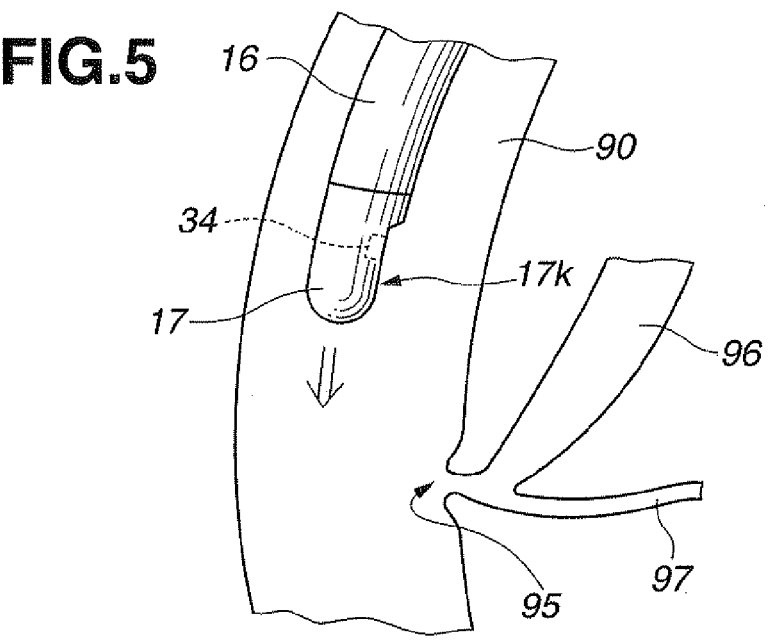
FIG. 5 is a view showing a state where a distal end portion of an endoscope insertion portion of FIG. 1 is inserted into a duodenum.
Figure 6:
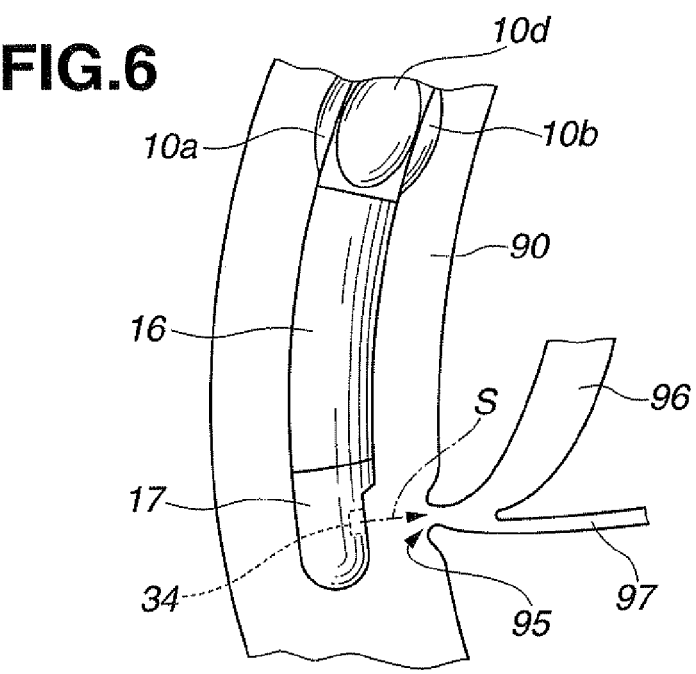
FIG. 6 is a view showing a state where the distal end portion of the endoscope insertion portion of FIG. 1 is inserted into the vicinity of the papilla of the duodenum.
Figure 7:
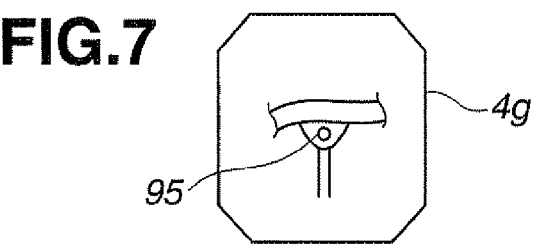
FIG. 7 is a view showing a monitor screen displaying an image of the papilla captured at the position in FIG. 6 by an objective lens of the distal end portion.

FIG. 5 is a view showing a state where a distal end portion of an endoscope insertion portion of FIG. 1 is inserted into the duodenum, FIG. 6 is a view showing a state where the distal end portion of the endoscope insertion portion of FIG. 1 is inserted in the vicinity of the papilla of the duodenum, and FIG. 7 is a view showing a monitor screen displaying an image of the papilla captured at the position in FIG. 6 by an objective lens of the distal end portion.

Figure 8:
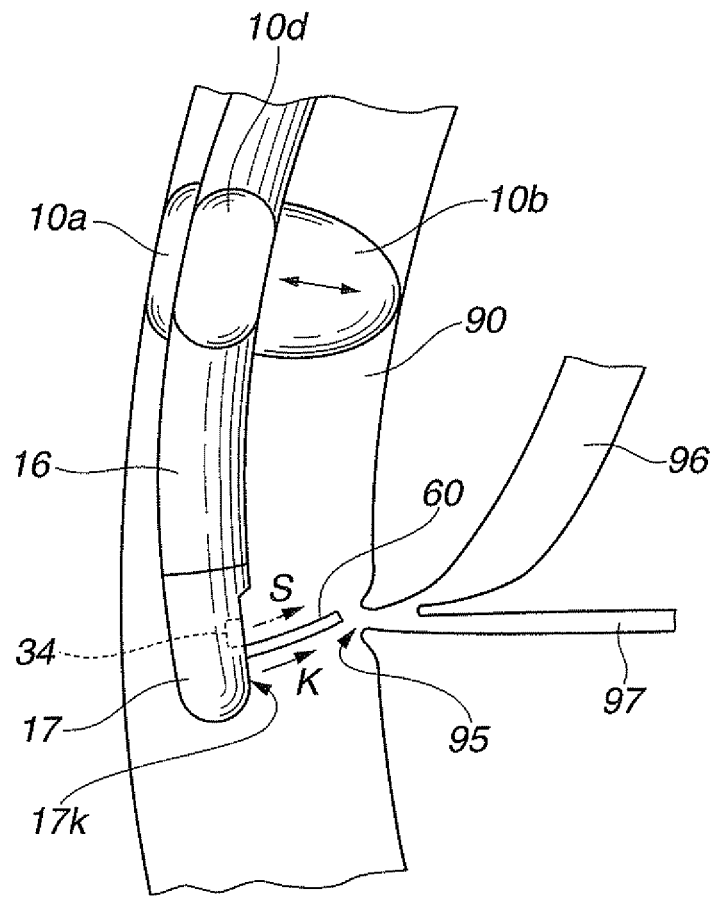
FIG. 8 is a view showing a state where a bending portion is fixed at the position in FIG. 6 and a treatment instrument is projected from a channel aperture portion.
Figure 9:
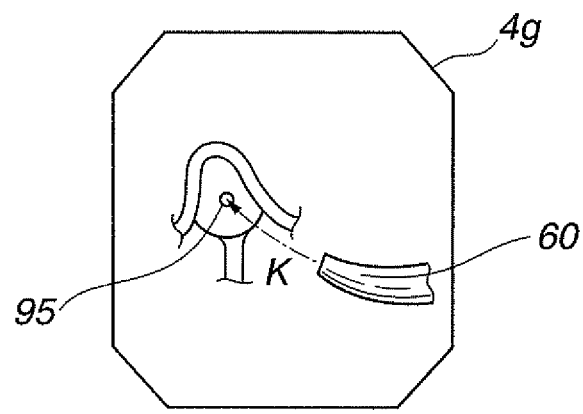
FIG. 9 is a view showing the monitor screen displaying an image of the papilla captured at the position in FIG. 8 by an objective lens of the distal end portion.
Figure 10:
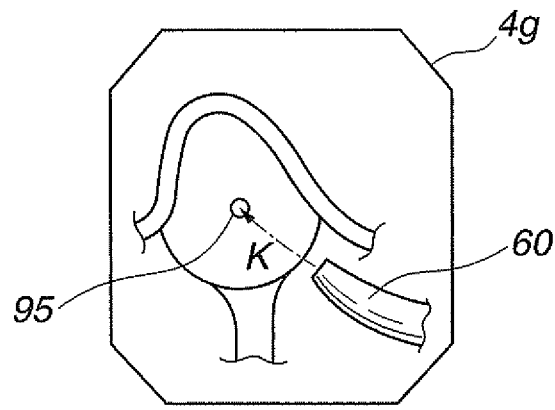
FIG. 10 is a view showing the monitor screen in a state where the distal end portion is moved in parallel in a direction close to the papilla while the treatment instrument is projected, and the distal end of the treatment instrument is brought close to the papilla.
Figure 11:
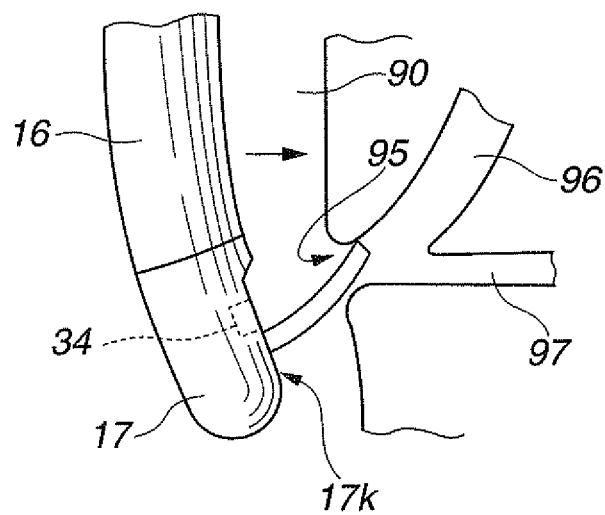
FIG. 11 is a view showing a state where the distal end portion is further moved in parallel in the direction close to the papilla to push up an upper side of the papilla by the distal end of the treatment instrument.

Furthermore, FIG. 8 is a view showing a state where the bending portion is fixed at the position in FIG. 6 and the treatment instrument is projected from a channel aperture portion, FIG. 9 is a view showing the monitor screen displaying an image of the papilla captured at the position in FIG. 8 by the objective lens of the distal end portion, FIG. 10 is a view showing the monitor screen displaying an image of the papilla captured by the objective lens of the distal end portion in a state where the distal end portion is moved in parallel in a direction close to the papilla while the treatment instrument is projected, and the distal end of the treatment instrument is brought close to the papilla, and FIG. 11 is a view showing a state where the distal end portion is further moved in parallel in the direction close to the papilla to push up an upper side of the papilla by the distal end of the treatment instrument.

Figure 12:
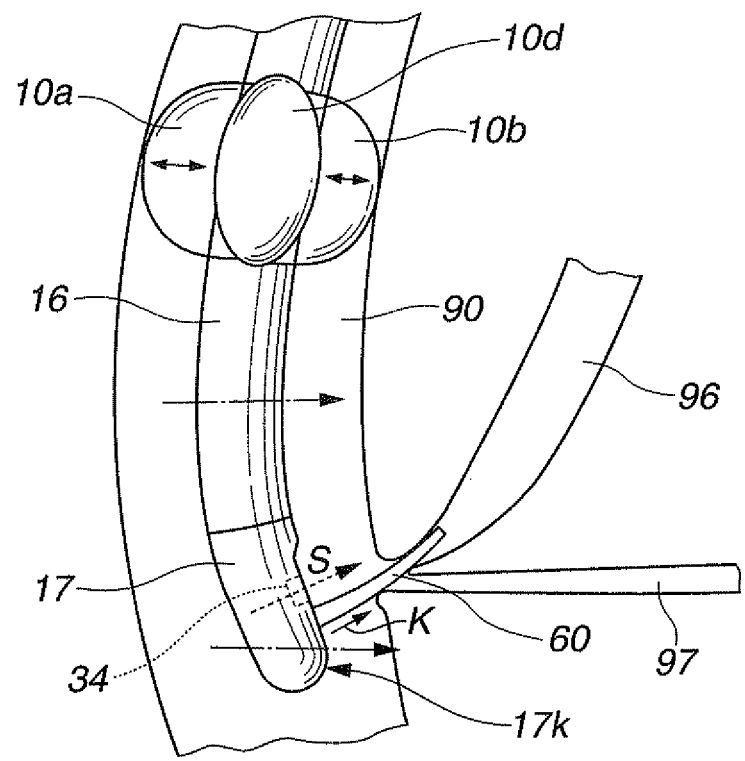
FIG. 12 is a view showing a state where the treatment instrument is inserted into the bile duct as a result of moving the distal end portion in parallel in the direction close to the papilla.
Figure 13:
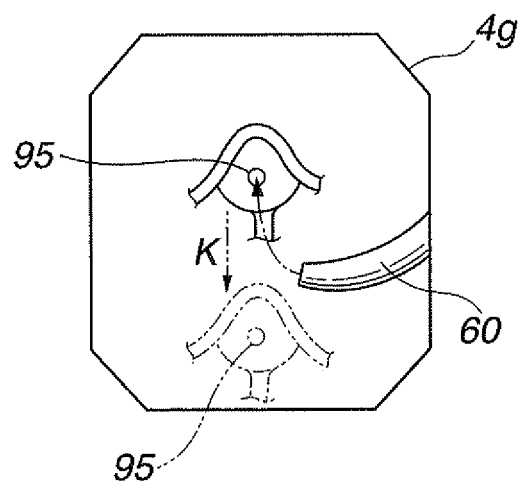
FIG. 13 is a view showing the monitor screen in a state where a conventional bending portion is bent to bring the distal end of the treatment instrument close to the papilla.
Figure 14:
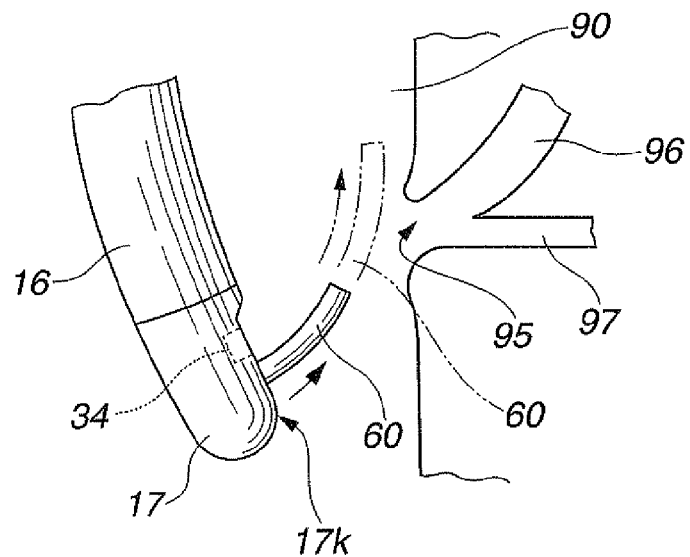
FIG. 14 is a view showing a state where a conventional treatment instrument is pushed in, to bring the distal end of the treatment instrument close to the papilla.

Furthermore, FIG. 12 is a view showing a state where the treatment instrument is inserted into the bile duct as a result of moving the distal end portion in parallel in the direction close to the papilla, FIG. 13 is a view showing the monitor screen displaying an image of the papilla captured by the objective lens of the distal end portion in a state where the conventional bending portion is bent to bring the distal end of the treatment instrument close to the papilla, and FIG. 14 is a view showing a state where a conventional treatment instrument is pushed in, to bring the distal end of the treatment instrument close to the papilla.

First, as shown in FIG. 5, the insertion portion 12 of the endoscope 1 is inserted into the duodenum 90 by push-in operation of the insertion portion 12 by an operator, and thereafter, as shown in FIGS. 6,7, the insertion portion 12 is pushed in until the objective lens 34, which is disposed in the distal end portion 17 of the insertion portion 12, captures an image of the papilla 95 and the papilla 95 is displayed on the screen 4g of the monitor 4, and the bending portion 16 is bent by the operator operating a bending operation knob 35.

Note that, as a result, the second balloon 10b is located on the side close to the papilla 95 and the first balloon 10a is located on the side away from the papilla 95 in the duodenum 90. Furthermore, the third balloon 10c is located on the left side with respect to the papilla 95 and the fourth balloon 10d is located on the right side with respect to the papilla 95.

Next, as shown in FIGS. 8, 9, from the channel aperture portion 27 of the distal end portion 17 is projected by the operator the distal end side of the catheter 60 inserted into the treatment instrument insertion channel from the aperture 40a of the treatment instrument insertion port 40, and then a bending angle of the projected bending portion 16 is fixed.

This causes a projecting direction K, which is an insertion direction of the catheter 60 projected from the channel aperture portion 27, to be fixed. Note that the projecting direction K is fixed so as to be the same as the field of view direction S of the objective lens 34 at this time.

In this state, as shown in FIG. 8, when the on-button of the proximal-side switch 5b of the foot switch 5 is depressed by the operator, air is sent from the air feeding/sucking device 71 to the second balloon 10b via the balloon conduit 11b. Note that the air is continued to be fed to the second balloon 10b until the depression of the on-button of the proximal-side switch 5b is released.

As a result, the second balloon 10b is pressurized to be inflated, and the second balloon 10b and the first balloon 10a contact the intestinal wall of the duodenum 90, thereby fixing the insertion portion 12 to the duodenum 90, with the objective lens 34 capturing the papilla 95. In other words, the insertion portion 12 is fixed to the duodenum 90 without the field of view direction S changed.

Next, when the off-button of the proximal-side switch 5b of the foot switch 5 is depressed and the on-button of the distal-side switch 5a of the foot switch 5 is also depressed, air is sucked from the second balloon 10b via the balloon conduit 11b and air is fed to the first balloon 10a via the balloon conduit 11a.

Note that air is sucked from the second balloon 10b while the off-button of the proximal-side switch 5b is depressed, and air is fed to the first balloon 10a while the on-button of the distal-side switch 5a is depressed. In addition, it is preferable that the air suction amount from the second balloon 10b and the air feeding amount to the first balloon 10a are the same.

As a result, the second balloon 10b is contracted by depressurization and the first balloon 10a is inflated by pressurization, thereby moving the one-side surface 17k of the distal end portion 17 in parallel with respect to the field of view direction S toward the direction close to the papilla 95, which is a diameter direction of the distal end portion 17, parallel to the field of view direction S of the objective lens 34, then as shown in FIG. 10, the papilla 95 is displayed in an enlarged manner on the monitor screen 4g.

Note that, since the bending angle of the bending portion 16 is fixed and the one-side surface 17k of the distal end portion 17 is moved parallel with respect to the field of view direction S when the one-side surface 17k is brought close to the papilla 95, the field of view direction S of the objective lens 34 or the insertion direction K of the catheter 60 before the movement shown in FIG. 9 and the field of view direction S of the objective lens 34 or the insertion direction K of the catheter 60 after the parallel movement shown in FIG. 10 are the same.

Therefore, unlike a conventional example in which the bending portion 16 is bent to bring the one-side surface 17k close to the papilla 95 as shown in FIG. 13, the distal end of the catheter 60 does not deviate in up/down direction with respect to the papilla 95 before and after the movement. That is, the one-side surface 17k is brought close to the papilla 95 while maintaining the field of view direction S and the insertion direction K.

Subsequently, when the second balloon 10b is continued to be contracted and the first balloon 10a is continued to be inflated by predetermined operations, the one-side surface 17k is brought closer to the papilla 95 by the parallel movement. As a result, as shown in FIG. 11, on the screen 4g, the upper side of the papilla 95 is pushed up by the distal end portion of the catheter 60 projected from the channel aperture portion 27.

Note that, in this position, in order to accurately and surely make the distal end side of the catheter 60 contact the upper side of the papilla 95, the above-described treatment instrument raising table may be operated or the bending portion 16 may be bent again by the operator.

After that, the second balloon 10b is further continued to be contracted and the first balloon 10a is continued to be inflated by predetermined operations, thereby moving the one-side surface 17k in parallel with respect to the field of view direction S toward the direction close to the papilla. As a result, as shown in FIG. 12, the distal end portion side of the catheter 60 projecting from the channel aperture portion 27 is inserted into the bile duct 96. Note that, after that, the proximal end side of the catheter 60 is pushed in by the operator, thereby allowing the distal end portion side of the catheter 60 to be advanced in the bile duct 96.

Since the catheter 60 is thus inserted into the bile duct 96, unlike the conventional case shown in FIG. 14 where the catheter 60 is pushed to be inserted into the bile duct 96 via the papilla 95 by the operator, there is not such a problem that the distal end of the catheter 60 does not enter the papilla 95 and deviates upward from the papilla 95 on the screen 4g, for example, due to the tendency to bending applied to the catheter 60 by the treatment instrument raising table and the like as a result of having undergone several cases.

Next, with reference to FIGS. 15 to 22, description will be made on an insertion method of the catheter 60 into the papilla 95 in a case where, after the insertion portion 12 of the endoscope 1 is inserted in the vicinity of the papilla 95 by the push-in operation of the insertion portion 12 into the duodenum 90 by the operator, the distal end portion 17 of the insertion portion 12 is displayed deviated to the right side on the screen 4g with respect to the papilla 95.

Figure 15:
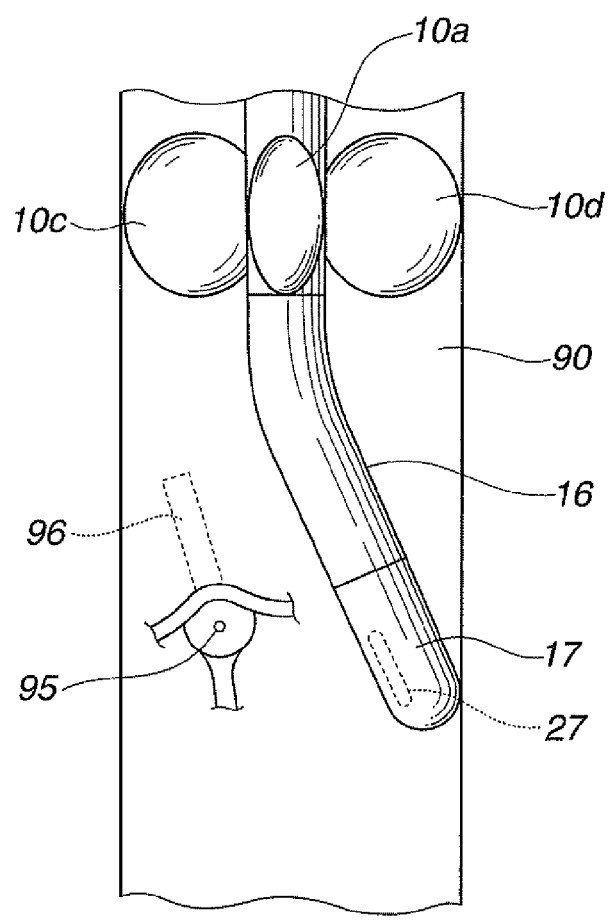
FIG. 15 is a view showing a state where the distal end portion of the endoscope insertion portion is inserted into a position in the vicinity of the papilla of the duodenum, deviated to right with respect to the papilla.
Figure 16:
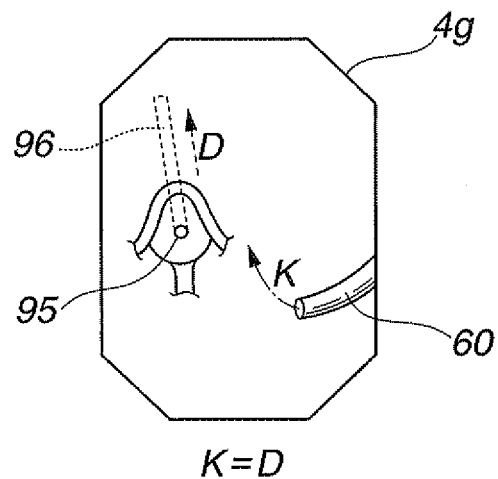
FIG. 16 is a view showing the monitor screen displaying an image of the papilla captured at the position in FIG. 15 by the objective lens of the distal end portion.
Figure 17:
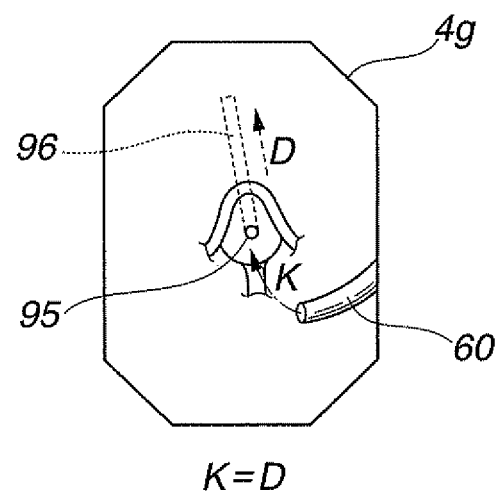
FIG. 17 is a view showing the monitor screen in a state where the distal end portion is moved in parallel in the left direction while the treatment instrument is projected from the channel aperture portion, to bring the distal end of the treatment instrument close to the papilla.

FIG. 15 is a view showing a state where the distal end portion of the endoscope insertion portion is inserted into a position in the vicinity of the papilla of the duodenum deviated to right with respect to the papilla, FIG. 16 is a view showing the monitor screen displaying an image of the papilla captured at the position in FIG. 15 by the objective lens of the distal end portion, and FIG. 17 is a view showing the monitor screen displaying an image of the papilla captured by the objective lens of the distal end portion in a state where the distal end portion is moved in parallel in the left direction while the treatment instrument is projected from the channel aperture portion, to bring the distal end of the treatment instrument close to the papilla.

Figure 18:
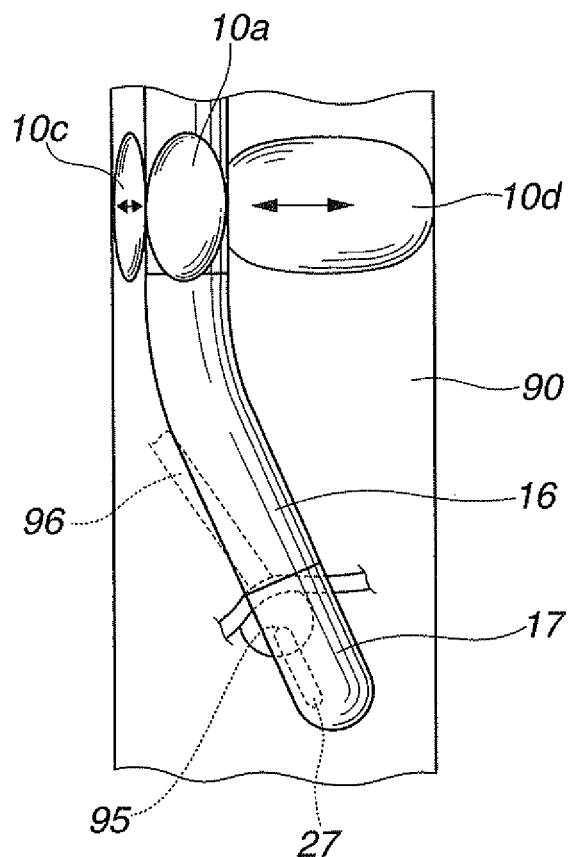
FIG. 18 is a view showing a state where the treatment instrument is inserted from the papilla into the bile duct after the distal end portion is moved in parallel to the left direction.
Figure 19:
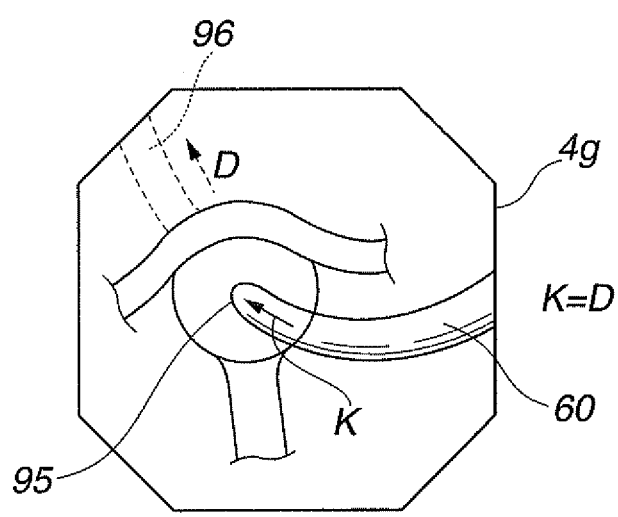
FIG. 19 is a view showing the monitor screen displaying an image of the papilla captured at the position in FIG. 18 by the objective lens of the distal end portion.

Furthermore, FIG. 18 is a view showing a state where the treatment instrument is inserted from the papilla into the bile duct after the distal end portion is moved in parallel in the left direction, and FIG. 19 is a view showing the monitor screen displaying an image of the papilla captured at the position in FIG. 18 by the objective lens of the distal end portion.

Figure 20:
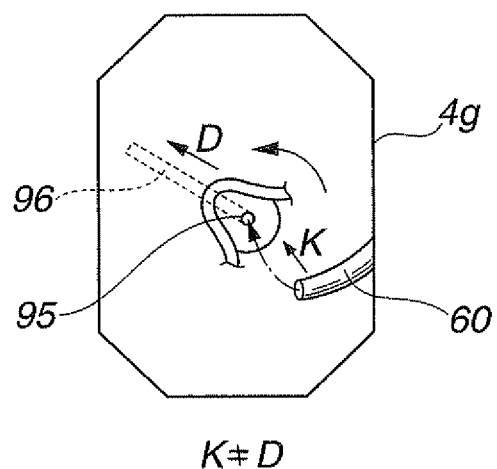
FIG. 20 is a view showing the monitor screen in a state where the conventional bending portion is bent and the distal end of the treatment instrument is bent to be moved in the left side to bring the distal end of the treatment instrument close to the papilla.
Figure 21:
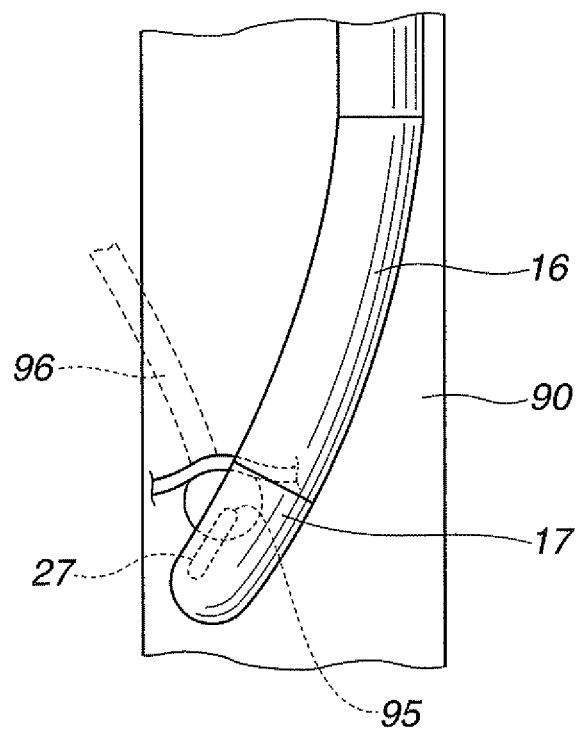
FIG. 21 is a view showing a state where the treatment instrument is inserted from the papilla into the bile duct after bending and moving the conventional distal end portion in the left direction.
Figure 22:
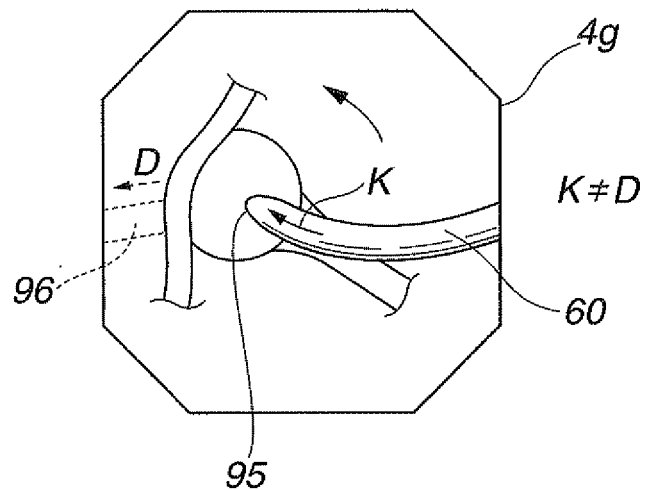
FIG. 22 is a view showing a monitor screen displaying an image of the papilla captured at the position in FIG. 21 by the objective lens of the distal end portion.

In addition, FIG. 20 is a view showing a monitor screen displaying an image of the papilla captured by the objective lens of the distal end portion in a state where the conventional bending portion is bent and the distal end of the treatment instrument is bent to be moved in the left side to bring the distal end of the treatment instrument close to the papilla, FIG. 21 is a view showing a state where the treatment instrument is inserted from the papilla into the bile duct after bending and moving the conventional distal end portion in the left direction, and FIG. 22 is a view showing a monitor screen displaying an image of the papilla captured at the position in FIG. 21 by the objective lens of the distal end portion.

First, as shown in FIG. 15, the insertion portion 12 of the endoscope 1 is inserted into the duodenum 90 by push-in operation of the insertion portion 12 by the operator to reach in the vicinity of the papilla 95, and then, as shown in FIG. 16, when the distal end portion 17 of the insertion portion 12 is displayed deviated to the right side on the screen 4g with respect to the papilla 95, the distal end of the catheter 60 is projected from the channel aperture portion 27 and also the bending angle of the bending portion 16 is operated to be adjusted so that the projecting direction K which is the insertion direction of the catheter 60 and a direction D of the bile duct 96 coincide with each other by the operator.

Note that, also in this case, the second balloon 10b is located on the side close to the papilla 95 and the first balloon 10a is located on the side away from the papilla 95 in the duodenum 90. In addition, the third balloon 10c is located on the left side with respect to the papilla 95 and the fourth balloon 10d is located on the right side with respect to the papilla 95.

Next, the bending angle of the bending portion 16 is fixed and then the on-buttons of the left-side switch 5c and the right-side switch 5d of the foot switch 5 are depressed by the operator, thereby causing the air feeding/sucking device 71 to feed air to the third balloon 10c and the fourth balloon 10d via the balloon conduits 11c. 11d.

Note that air is fed to the third balloon 10c and the fourth balloon 10d while the on-buttons of the left-side switch 5c and the right-side switch 5d are continued to be depressed.

As a result, the third balloon 10c and the fourth balloon 10d are inflated, and the third balloon 10c and the fourth balloon 10d contact the intestinal wall of the duodenum 90, thereby fixing the insertion portion 12 to the duodenum 90.

After that, the off-switch of the left-side switch 5c of the foot switch 5 is depressed by the operator, thereby sucking air from the third balloon 10c via the balloon conduit 11c, and the on-button of the right-side switch 5d of the foot switch S is depressed by the operator, thereby feeding air to the fourth balloon 10d via the balloon conduit 11d. As a result, the third balloon 10c is contracted by depressurization and the fourth balloon 10d is inflated by pressurization.

Note that air is sucked from the third balloon 10c while the off-button of the left-side switch 5c is depressed, and air is fed to the fourth balloon 10d while the on-button of the right-side switch 5d is depressed. In addition, it is preferable that the air suction amount from the third balloon 10c and the air feeding amount to the fourth balloon 10d are the same.

As a result, the one-side surface 17k of the distal end portion 17 is moved in parallel with respect to the field of view direction S, in the left direction with respect to the papilla 95, which is a diameter direction of the distal end portion 17, parallel to the field of view direction S of the objective lens 34.

Note that the parallel movement, in other words, the contraction of the third balloon 10c and the inflation of the fourth balloon 10d are continued until the distal end of the catheter 60 and the papilla 95 come close to each other on the monitor screen 4g, as shown in FIG. 17.

In addition, since the bending angle of the bending portion 16 is fixed and the one-side surface 17k of the distal end portion 17 is moved to left side in parallel to the field of view direction S when the one-side surface 17k is brought close to the papilla 95, the field of view direction S of the objective lens 34 or the insertion direction K of the catheter 60 before the movement shown in FIG. 16 and the field of view direction S of the objective lens 34 or the insertion direction K of the catheter 60 after the parallel movement shown in FIG. 17 become the same.

That is, the insertion direction K of the catheter 60 and the direction D of the bile duct 96 do not deviate from each other before and after the movement. That is, the one-side surface 17k is brought close to the papilla 95 while maintaining the field of view direction S and the insertion direction K.

Therefore, unlike a conventional example shown in FIG. 21 in which the bending portion 16 is bent and the one-side surface 17k is moved to left side to bring the one-side surface 17k close to the papilla 95, there is not such a problem shown in FIGS. 20, 22 that the insertion of the catheter 60 into the bile duct 96 becomes difficult by the field of view with respect to the papilla 95 being inclined on the screen 4g and the insertion direction K of the catheter 60 and the direction D of the bile duct 96 being deviated from each other before and after the movement.

Finally, as shown in FIGS. 18, 19, the catheter 60 is pushed in by the operator and inserted into the bile duct 96 in a state where the one-side surface 17k and the papilla 95 are brought close to each other. At this time, since the insertion direction K of the catheter 60 and the direction D of the bile duct 96 are coincided with each other, the catheter 60 is easily inserted into the bile duct 96.

Note that the insertion of the catheter 60 into the bile duct 96 in a state where the one-side surface 17k is brought close to the papilla 95 by the movement in the left direction may be performed by contracting the second balloon 10b contacting the duodenum 90 and inflating the first balloon 10a, as shown in FIGS. 8 to 10, and 12.

In addition, though not shown, when the distal end portion 17 of the insertion portion 12 of the endoscope 1 is displayed deviated to the left side on the screen 4g with respect to the papilla, by inflating the third balloon 10c by pressurization and by contracting the fourth balloon 10d by depressurization, the one-side surface 17k of the distal end portion 17 is moved in parallel with respect to the field of view direction S toward the right side with respect to the papilla 95 to be brought close to the papilla 95 while maintaining the insertion direction K of the catheter 60 and the direction D of the bile duct 96 coincide with each other, similarly as the case described above.

Note that the above-described working is the same as in the case where the catheter 60 is inserted into a pancreatic duct 97 via the papilla 95. In that case, when bending the bending portion 16 before the parallel movement of the distal end portion 17 in the diameter direction, the projecting direction K which is the insertion direction of the catheter 60 projecting from the channel aperture portion 27 and the direction of the pancreatic duct 97 have only to be coincided with each other.

Thus, the present embodiment has shown that, the four balloons 10a to 10d are provided on the outer circumference of the distal end portion 15s of the flexible tube portion 15 provided to the insertion portion 12 of the endoscope 1, and after the insertion portion 12 is inserted into the duodenum 90 to ensure the field of view of the endoscope, only by inflating and contracting each of the balloons 10a to 10d, the one-side surface 17k of the distal end portion 17 is moved in parallel with respect to the papilla 95, separately from the bending of the bending portion 16, in the diameter direction of the distal end portion 17 parallel to the field of view direction S of the objective lens 34.

With this configuration, when the one-side surface 17k is brought close to the papilla, the one-side surface 17k can be easily brought to close to the papilla while maintaining the previously ensured field of view before the movement, in other words, without changing the field of view direction S of the objective lens 34, thereby facilitating the insertion of the catheter 60 into the papilla.

In addition, each of the balloons 10a to 10d is disposed on the distal end portion 15s of the flexible tube portion 15, in other words, not disposed on the distal end portion 17, which prevents the deviation of the field of view direction S due to inflation/contraction of each of the balloons 10a to 10d with respect to the papilla and hindrance of the field of view of the objective lens 34 due to contact with the papilla 95 after ensuring the field of view.

Furthermore, since each of the balloons 10a to 10d is not disposed on the bending portion 16, when fine adjustment by bending operation of the bending portion is needed after inflation/contraction of each of the balloons 10a to 10d, the bending angle of the bending portion 16 can be changed again even after inflation/contraction of each of the balloons 10a to 10d. In addition, deformation of wire of the bending portion 16 by the inflation/contraction of each of the balloons 10a to 10d and resultant deviation of the moving direction of the one-side surface 17k of the distal end portion 17 are prevented.

Figure 23:
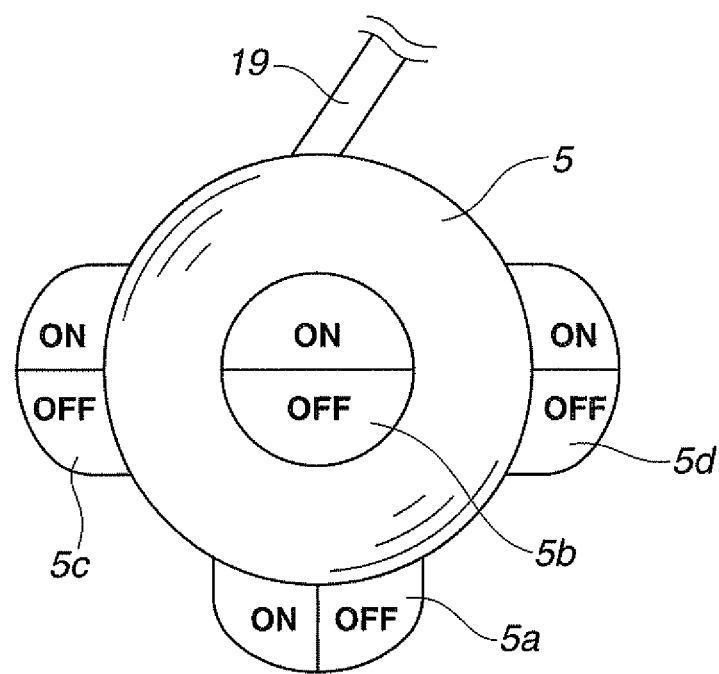
FIG. 23 is a perspective view showing a modified example of a foot switch of FIG. 1.

Note that modified examples are shown below, FIG. 23 is a perspective view showing a modified example of the foot switch of FIG. 1.

As shown in FIG. 23, the switch for instructing to feed and suck air to and from each of the balloons 10a to 10d is not limited to a foot switch, and the switch may be a spherical holding switch to be held and operated by the operator, for example. Note that the shape of the holding switch is not limited a spherical shape.

Note that another modified example is shown below.

Figure 24:
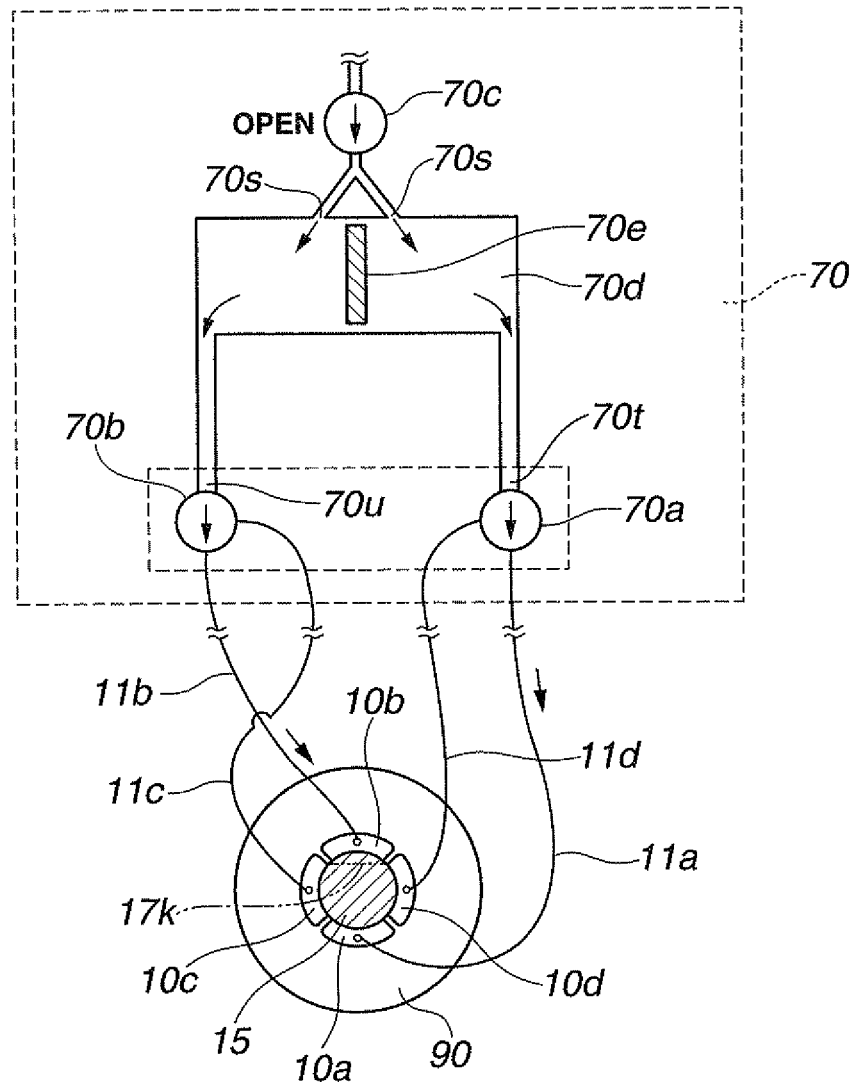
FIG. 24 is a view showing an expansion/contraction mechanism for inflating and contracting a first balloon interlockingly with a second balloon, or a third balloon interlockingly with a fourth balloon.
Figure 25:
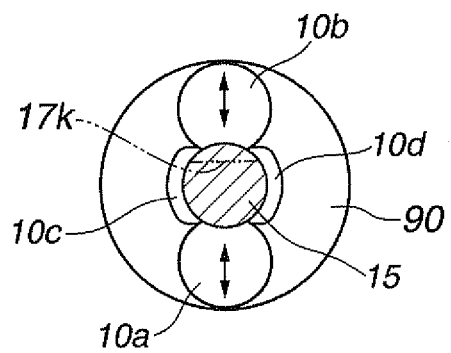
FIG. 25 is a cross-sectional view showing a state where the insertion portion is fixed to the duodenum by interlockingly inflating the second balloon and the first balloon of FIG. 24.
Figure 26:
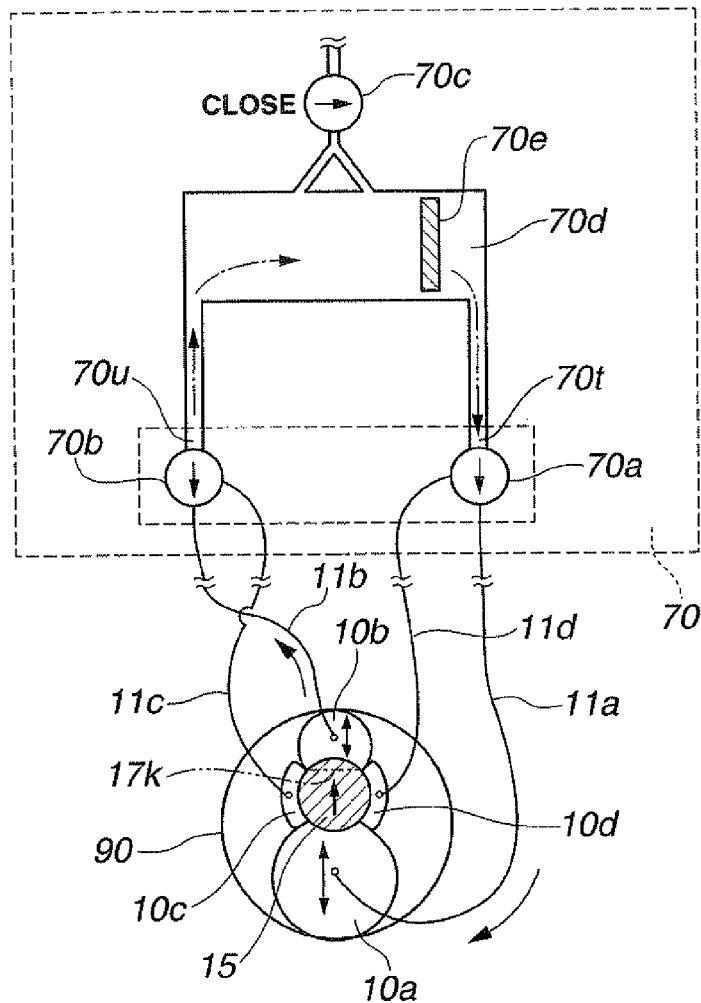
FIG. 26 is a view showing a state of a piston of the expansion/contraction mechanism at the time of inflating the first balloon of FIG. 25 interlockingly with the second balloon being contracted.

FIG. 24 is a view showing an expansion/contraction mechanism for inflating and contracting a first balloon interlockingly with a second balloon, or a third balloon interlockingly with a fourth balloon, FIG. 25 is a cross-sectional view showing a state where the insertion portion is fixed to the duodenum by interlockingly inflating the second balloon and the first balloon of FIG. 24, and FIG. 26 is a view showing a state of a piston of the expansion/contraction mechanism at the time of inflating the first balloon of FIG. 25 interlokingly the second balloon being contracted.

Figure 27:
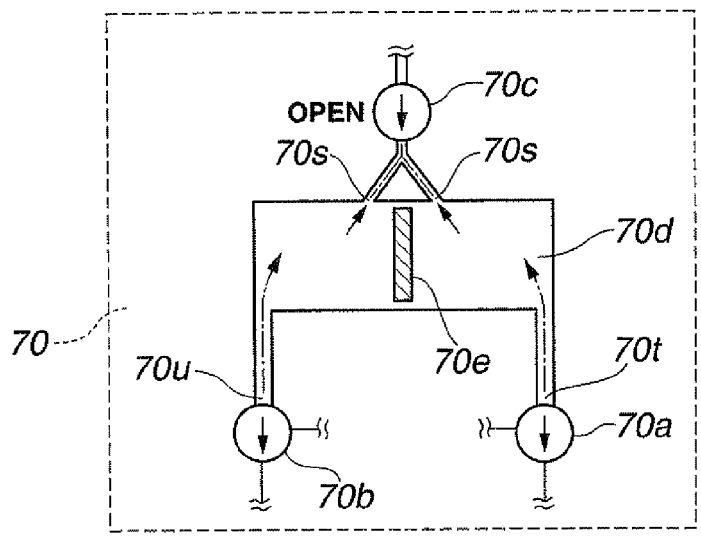
FIG. 27 is a view showing a state of a valve of the expansion/contraction mechanism when air is exhausted from the second balloon and the first balloon of FIG. 26.
Figure 28:
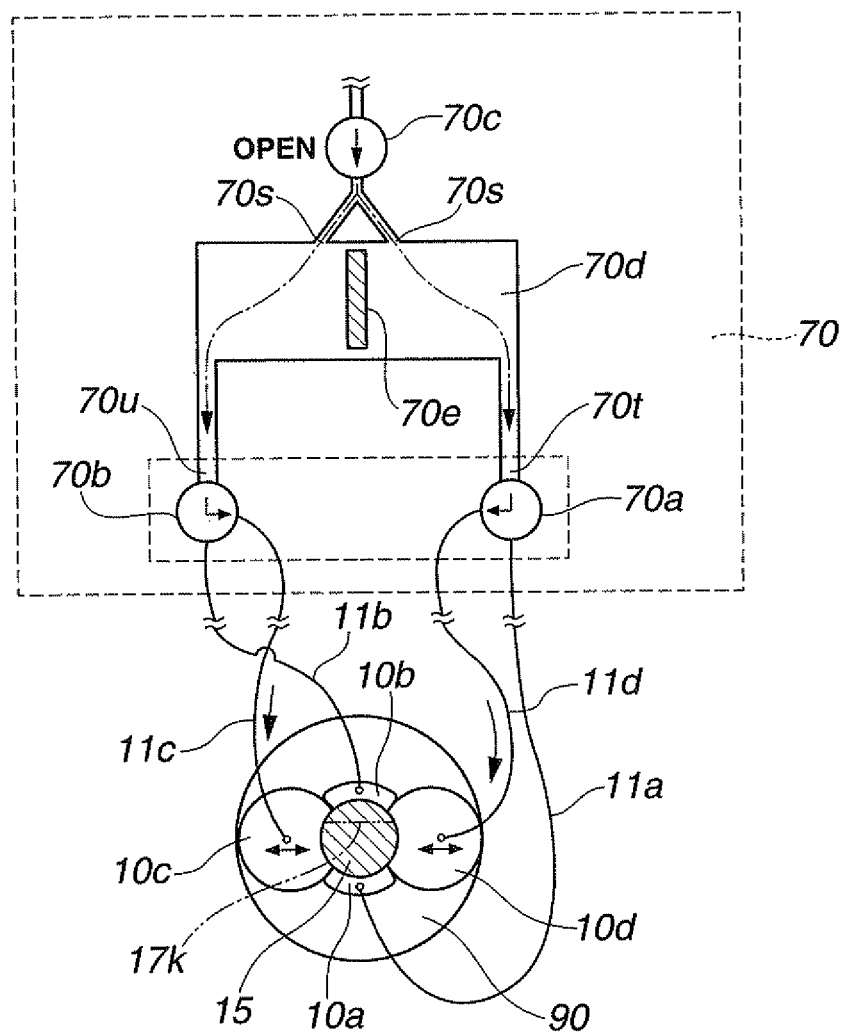
FIG. 28 is a view showing a state of the valve of the expansion/contraction mechanism at the time of fixing the insertion portion to the duodenum by interlockingly inflating the third balloon and the fourth balloon of FIG. 24.
Figure 29:
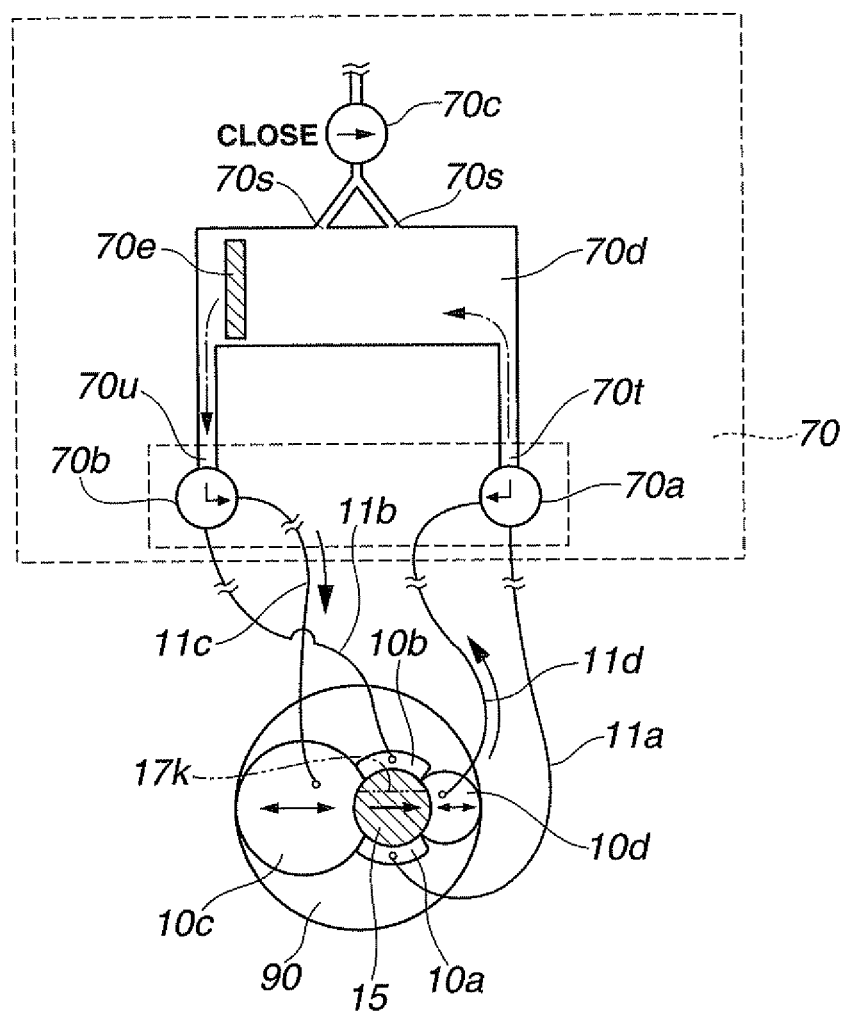
FIG. 29 is a view showing a state of the piston of the expansion/contraction mechanism at the time of inflating the third balloon of FIG. 28 interlockingly with the fourth balloon being contracted.

Furthermore, FIG. 27 is a view showing a state of a valve of the expansion/contraction mechanism when air is exhausted from the second balloon and the first balloon of FIG. 26, FIG. 28 is a view showing a state of the valve of the expansion/contraction mechanism at the time of fixing the insertion portion to the duodenum by interlockingly inflating the third balloon and the fourth balloon of FIG. 24, and FIG. 29 is a view showing a state of the piston of the expansion/contraction mechanism at the time of inflating the third balloon FIG. 28 interlockingly with the fourth balloon of being contracted.

In the present embodiment, each of the balloons 10a to 10d is individually inflated and contracted by air being fed or sucked by the air feeding/sucking device 71 to and from each of the balloon conduits 11a to 11d respectively connected to the balloons, only while on- or off-button of the foot switch 5 is continued to be depressed.

The configuration is not limited to the above, and the opposing second balloon 10b and the first balloon 10a, or the opposing third balloon 10c and the fourth balloon 10d may be inflated and contracted interlockingly with each other.

For example, when the one-side surface 17k of the distal end portion 17 of the insertion portion 12 is brought close to the papilla 95, the first balloon 10a may be inflated interlockingly with the second balloon 10b being contracted.

Showing a more specific configuration, as shown in FIG. 24, the balloon control unit 70 includes a syringe 70d configuring the expansion/contraction mechanism of the present invention. Note that the syringe 70d has inside a piston 70e movable from one end to the other end of the syringe 70d.

On the syringe 70d is open an introducing port 70s for air, to which a supply conduit extended from the air feeding/sucking device 71 is connected. Note that, in this case, a pump and the like for only feeding air is enough as the air feeding/sucking device 71. In addition, to the supply conduit is connected an air valve 70c for selectively changing over whether or not to introduce air into the syringe 70d.

Furthermore, the syringe 70d has on one end side thereof a supply port 70t for supplying air from the syringe 70d to the first balloon 10a and the fourth balloon 10d, and to the supply port 70t on the one end side is connected a first valve 70a.

Also, the syringe 70d has on the other end side thereof a supply port 70u for supplying air from the syringe 70d to the second balloon 10b and the third balloon 10c, and to the supply port 70u is connected a second valve 70b.

To the first valve 70a are connected the balloon conduit 11a communicated with the first balloon 10a and the balloon conduit 11d communicated with the fourth balloon 10d.

The first valve 70a supplies air supplied from the supply port 70t of the syringe 70d to either the balloon conduit 11a or the balloon conduit 11d by selectively changing over the conduits.

To the second valve 70b are connected the balloon conduit 11b communicated with the second balloon 10b and the balloon conduit 11c communicated with the third balloon 10c.

The second valve 70b supplies the air supplied from the supply port 70u of the syringe 70d to either the balloon conduit 11b or the balloon conduit 11c by selectively changing over the conduits.

Next, description will be made on a method of inflating and contracting the balloon interlockingly with the balloon opposing thereto by using the syringe 70d thus configured.

First, as described above, the insertion portion 12 is pushed into the duodenum 90 until the objective lens 34 disposed in the distal end portion 17 of the insertion portion 12 captures the image of the papilla 95 and the papilla 95 is displayed on the monitor screen 4g of the monitor 4, and when the insertion portion 12 is fixed to the duodenum 90, the air valve 70c is opened as shown in FIG. 24 and the first air valve 70a is changed over such that air is fed only to the balloon conduit 11a, and further the second valve 70b is changed over such that air is fed only to the balloon conduit 11b. Note that, in this case, the piston 70e is located at approximately the center between the one end side and the other end side of the syringe 70d, as shown in FIG. 24.

After that, when air is supplied from the air feeding/sucking device 71, the air is introduced into the syringe 70d from the introducing port 70s, and then fed to the balloon conduit 11a from the supply port 70t by the first valve 70a and also fed to the balloon conduit 11b from the supply port 70u by the second valve 70b.

As a result, as shown in FIG. 25, the second balloon 10b and the first balloon 10a are inflated by pressurization to contact the intestinal wall of the duodenum 90, thereby fixing the insertion portion 12 to the duodenum 90 with the objective lens 34 capturing the papilla 95.

Next, as shown in FIGS. 8 to 12, when the one-side surface 17k of the distal end portion 17 is brought close to the papilla 95 while keeping the field of view direction S of the objective lens 34 unchanged, the air valve 70c is closed and the piston 70e is moved in the syringe 70d to the one end side, that is, to the supply port 70t side, as shown in FIG. 26.

As a result, air is sucked by depressurization from the balloon 10b on the proximal side, and the sucked air is fed to the first balloon 10a via the balloon conduit 11b, the supply port 70u, inside of the syringe 70d, the supply port 70t, and the balloon conduit 11a.

Note that, at this time, the air valve 70c is closed, so that the amount of air sucked from the second balloon 10b and the amount of air fed to the first balloon 10a are the same.

Accordingly, the first balloon 10a is inflated by pressurization interlockingly with the second balloon 10b being contracted. Therefore, as described above, the one-side surface 17k of the distal end portion 17 is smoothly moved in parallel with respect to the field of view direction S toward the direction close to the papilla 95 which is a diameter direction of the distal end portion 17 parallel to the field of view direction S of the objective lens 34, and thereafter the catheter 60 projected from the channel aperture portion 27 is inserted into the bile duct 96 via the papilla 95.

After extracting the catheter 60 from the bile duct 96, when air is released from the second balloon 10b and the first balloon 10a, the air valve 70c is opened as shown in FIG. 27 after the piston 70e is returned to the approximately center position between one end side and the other end side in the syringe 70d as shown in FIG. 24.

As a result, air is released from the first balloon 10a, via the supply port 70t, the inside of the syringe 70d, the introducing port 70s, and the air valve 70c, and through the supply conduit, and also from the second balloon 10b, via the supply port 70u, the inside of the syringe 70d, the introducing port 70s, and air valve 70c, and through the supply conduit.

Next, description will be made on a method of inflating the third balloon 10e and contracting the fourth balloon 10d interlockingly with each other in a case where the insertion portion 12 of the endoscope 1 is inserted into the duodenum 90 by push-in operation of the insertion portion 12 by the operator to reach in the vicinity of the papilla 95, and thereafter the distal end portion 17 of the insertion portion 12 is, as described above, displayed deviated to the left side on the screen 4g with respect to the papilla 95.

First, the insertion portion 12 of the endoscope 1 is inserted by the operator into the duodenum 90 by push-in operation of the insertion portion 12. After the insertion portion 12 reaches in the vicinity of the papilla 95, in a case where the distal end portion 17 of the insertion portion 12 is displayed deviated to the left side with respect to the papilla 95 on the screen 4g, the distal end of the catheter 60 is projected from the channel aperture portion 27 and then the bending angle of the bending portion 16 is adjusted such that the projecting direction K which is the insertion direction of the catheter 60 coincides with the direction D of the bile duct 96. After that, the bending angle of the bending portion 16 is fixed by the operator.

Next, as shown in FIG. 28, the air valve 70c is opened, and the first valve 70a is changed over such that air is fed only to the balloon conduit 11d, and moreover, the second valve 70b is changed over such that air is fed only to the balloon conduit 11c. Note that, at this time, the piston 70e is located at approximately center between the one end side and the other end side in the syringe 70d, as shown in FIG. 28.

After that, when air is supplied from the air feeding/sucking device 71, the air is introduced from the introducing port 70s into inside of the syringe 70d, to be fed to the balloon conduit 11d from the supply port 70t by the first valve 70a, and also fed to the balloon conduit 11c from the supply port 70u by the second valve 70b.

As a result, as shown in FIG. 28, the third balloon 10c and the fourth balloon 10d are inflated by pressurization, to contact the intestinal wall of the duodenum 90, thereby fixing the insertion portion 12 to the duodenum 90 with the objective lens 34 capturing the papilla 95.

Subsequently, as shown in FIG. 29, the air valve 70c is closed and the piston 70e is moved inside of the syringe 70d to the other end side, that is, the supply port 70u side.

As a result, air is sucked from the right side balloon 10d by depressurization, and the sucked air is fed to the third balloon 10c via the balloon conduit 11d, the supply port 70t, the inside of the syringe 70d, the supply port 70u, and the balloon conduit 11c.

Note that, since the air valve 70c is closed at this time, the amount of air sucked from the fourth balloon 10d and the amount of air fed to the third balloon 10c are the same.

Accordingly, the third balloon 10c is inflated by pressurization interlockingly with the fourth balloon 10d being contracted. As a result, the one-side surface 17k of the distal end portion 17 is smoothly moved in parallel with respect to the field of view direction S toward the right direction with respect to the papilla 95, which is a diameter direction of the distal end portion 17, parallel to the field of direction S of the objective lens 34.

Note that, when the one-side surface 17k of the distal end portion 17 is moved in parallel in the left direction, similarly, it is only necessary that the air is moved by moving the piston 70e to the one end side such that the fourth balloon 10d is inflated and the third balloon 10c is contracted.

As described above, if inflation and contraction of the opposing first balloon 10a and the second balloon 10b, or the opposing third balloon 10c and the fourth balloon 10d are performed interlockingly with each other, the one-side surface 17k of the distal end portion 17 can be moved in parallel with respect to the field of view direction S more smoothly than in the above described present embodiment.

Note that another modified example is shown below.

Figure 30:
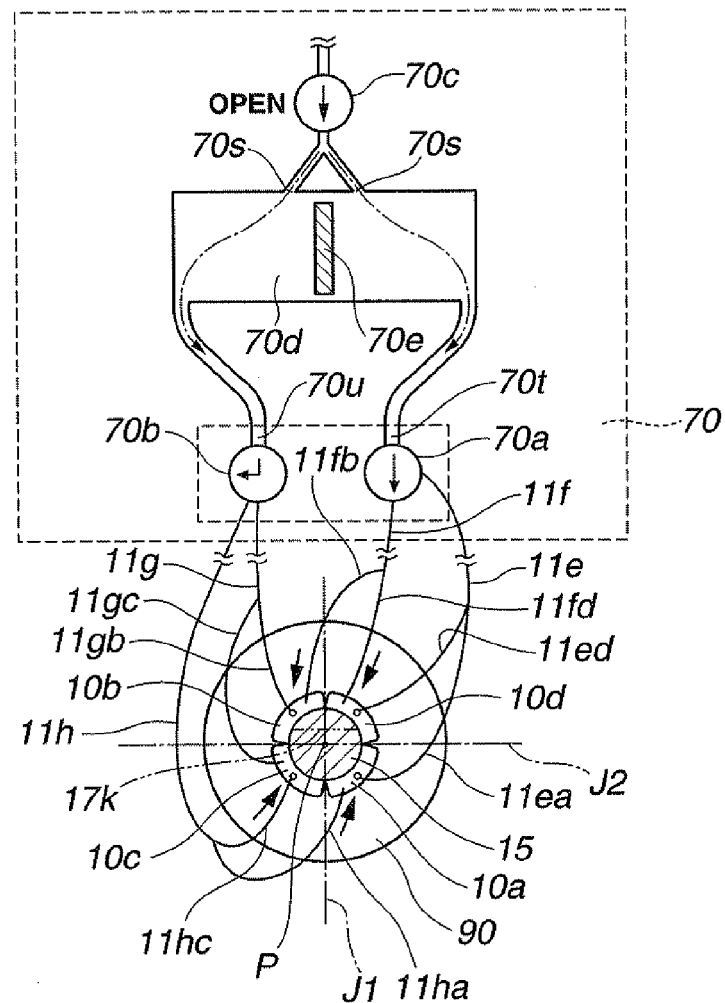
FIG. 30 is a view showing a modified example of the arrangement of the first to fourth balloons of FIG. 2 together with the expansion/contraction mechanism for inflating and contracting the first to fourth balloons interlockingly with one another.
Figure 31:
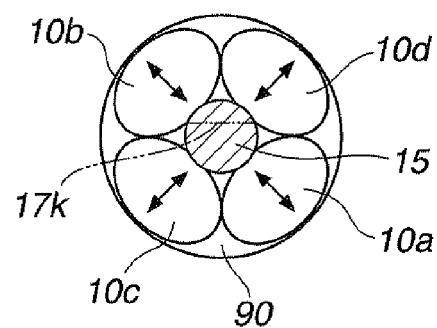
FIG. 31 is a cross-sectional view showing a state where the insertion portion is fixed to the duodenum by inflating the first to fourth balloons in FIG. 30 interlockingly with one another.

FIG. 30 is a view showing a modified example of the arrangement of the first to fourth balloons of FIG. 2 together with the expansion/contraction mechanism for inflating and contracting the first to fourth balloons interlockingly with one another, and FIG. 31 is a cross-sectional view showing a state where the insertion portion is fixed to the duodenum by inflating the first to fourth balloons in FIG. 30 interlockingly with one another.

Figure 32:
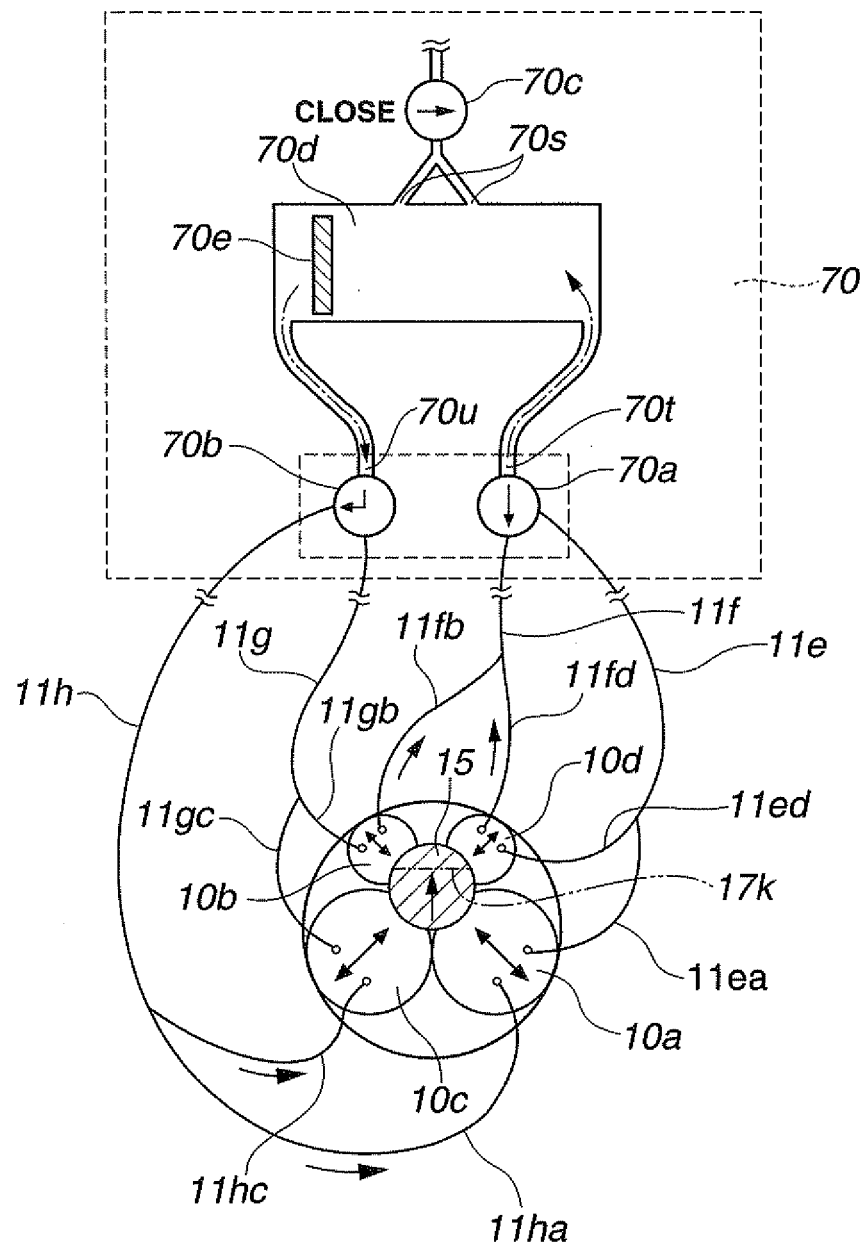
FIG. 32 is a view showing a state of the valve of the expansion/contraction mechanism at the time of inflating the first and the third balloons of FIG. 30 interlockingly with the second and the fourth balloons being contracted.
Figure 33:
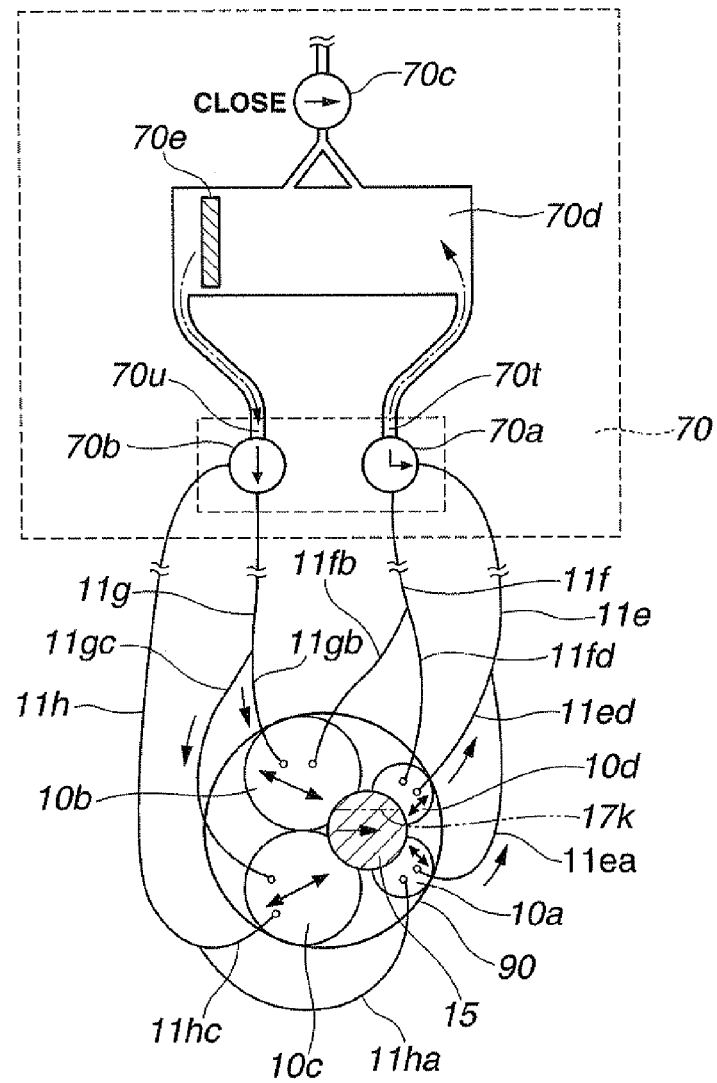
FIG. 33 is a view showing a state of the valve of the expansion/contraction mechanism at the time of inflating the second and the third balloons of FIG. 30 interlockingly with the first and the fourth balloons being contracted.

Furthermore, FIG. 32 is a view showing a state of the valve of the expansion/contraction mechanism at the time of inflating the first and the third balloons of FIG. 30 interlockingly with the second and the fourth balloons being contracted, and FIG. 33 is a view showing a state of the valve of the expansion/contraction mechanism at the time of inflating the second and the third balloons of FIG. 30 interlockingly with the first and the fourth balloons being contracted.

Figure 34:
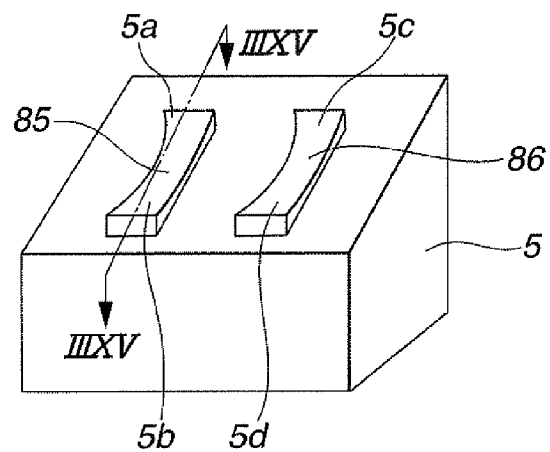
FIG. 34 is a perspective view showing a modified example of a foot switch shown in FIG. 2.
Figure 35:
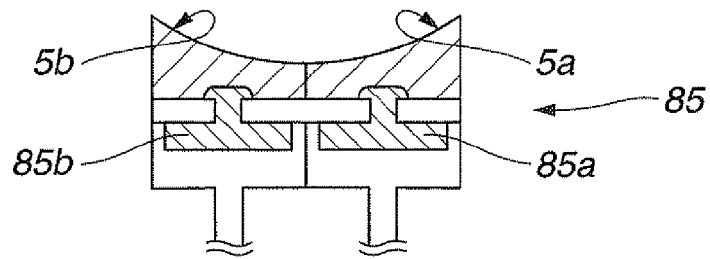
FIG. 35 is a cross-sectional view along the IIIXV-IIIXV line of FIG. 34.
Figure 36:
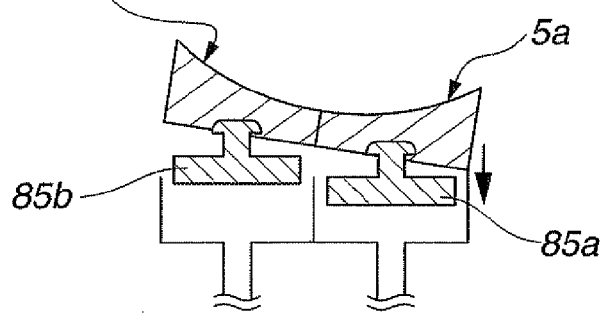
Figure 37:
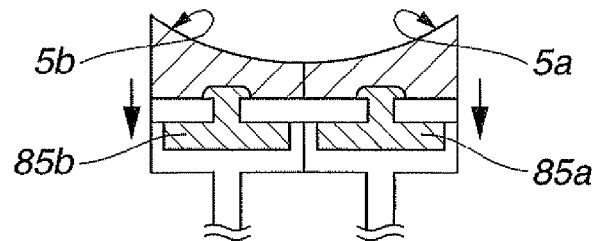

Moreover, FIG. 34 is a perspective view showing a modified example of the foot switch shown in FIG. 2, FIG. 35 is a cross-sectional view along the IIIXV-IIIXV line of FIG. 34, FIG. 36 is a cross-sectional view showing a state where a distal-side switch of FIG. 35 is turned on, and FIG. 37 is a cross-sectional view showing a state where the distal-side switch and a proximal-side switch of FIG. 35 are turned on.

Note that, the configuration of the syringe 70d is the same as that of the syringe 70d shown in FIGS. 24 to 29, so that the description thereof will be omitted.

The above-described present embodiment, as shown in FIG. 2, showed that the second balloon 10b is disposed on the outer circumferential surface of the distal end portion 15s of the flexible tube portion 15 so as to be located at a position on the first axis J1, which is on the field of direction S side, in other words, on the side where the one-side surface 17k is formed, and the first balloon 10a is disposed at a position on the first axis J1, which is on the opposite direction side of the field of view direction S of the objective lens 34.

In addition, the above-described present embodiment showed that the third balloon 10c is disposed at a position on the second axis, which is on the one end side in the direction orthogonal to the field of view direction of the objective lens 34, and the fourth balloon 10d is disposed at a position on the second axis, which is on the other end side in the direction orthogonal to the field of view direction of the objective lens 34.

The positions of the balloons are not limited to the above, and as long as the balloons 10a to 10d are disposed at line-symmetric positions with respect to the first axis J1 or the second axis J2 so as to oppose to each other, the first balloon 10a and the third balloon 10c may be disposed at the line-symmetric positions with respect to the first axis J1 and the second balloon 10b and the fourth balloon 10d may be disposed at the line-symmetric positions with respect to the first axis J1, as shown in FIG. 30.

In this case, the first balloon 10a and the fourth balloon 10d are disposed at line-symmetric positions with respect to the second axis J2, and the second balloon 10b and the third balloon 10c are disposed at line-symmetric positions with respect to the second axis J2.

More specifically, the balloons 10b, 10d are disposed on the outer circumferential surface of the distal end portion 15s of the flexible tube portion 15 so as to be located on the side of the field of direction S of the objective lens 34, that is, on the side where the one-side surface 17k is formed, and the balloons 10c, 10a are disposed so as to be located on the opposite direction side of the field of view direction S of the objective lens 34.

In addition, the second balloon 10b and the third balloon 10c are disposed on the left side with respect to the papilla 95, for example, and the first balloon 10a and the fourth balloon 10d are disposed on the right side with respect to the papilla 95, for example.

Note that, in such an arrangement, when the endoscope 1 is inserted into the body cavity to observe the papilla 95, the objective lens 34 is brought close to the region to be inspected, so that the second balloon 10b and the fourth balloon 10d are located on the side close to the papilla 95 and the first balloon 10a and the third balloon 10c are located on the side away from the papilla 95.

In addition, as shown in FIG. 30, the balloon conduits 11e, 11f are connected to the first valve 70a. The conduit le is diverged at a middle position thereof into conduits 11ea and 11ed, and the conduit 11ea and the conduit 11ed are connected to the first balloon 10a and the fourth balloon 10d, respectively.

In addition, the conduit 11f is diverged at a middle position thereof into conduits 11fb and 11fd, and the conduit 11bf and the conduit 11fd are connected to the second balloon 10b and the fourth balloon 10d, respectively.

The first valve 70a supplies the air supplied from the supply port 70t of the syringe 70d to either the balloon conduit 11e or the balloon conduit 11f by selectively changing over the conduits.

In addition, the balloon conduits 11g, 11h are connected to the second valve 70b. The conduit 11g is diverged at a middle position thereof into conduits 11gb and 11gc, and the conduit 11gb and the conduit 11gc are connected to the second balloon 10b and the third balloon 10c, respectively.

Furthermore, the conduit 11h is diverged at a middle position thereof into conduits 11ha and 11hc, and the conduit 11ha and the conduit 11hc are connected to the first balloon 10a and the third balloon 10c, respectively.

The second valve 70b supplies air supplied from the supply port 70u of the syringe 70d to either the balloon conduit 11g or the balloon conduit 11h by selectively changing over the conduits.

In addition, the foot switch 5, which inflates and contracts each of the balloons 10a to 10d thus disposed such that the respective opposing balloons inflate and contract interlockingly with each other, includes a switch 85 formed by integrating the distal-side switch 5a and the proximal-side switch 5b, and a switch 86 formed by integrating the left-side switch 5c and the right-side switch 5d, as shown in FIG. 34.

In addition, the switch 85 is provided with a contact 85a corresponding to the distal-side switch 5a and a contact 85b corresponding to the proximal-side switch 5b. As shown in FIG. 36, the contact 85b is turned off when the distal-side switch 5a is turned on to turn on the contact 85a. In addition, though not shown, the contact 85a is turned off when the contact 85b is turned on. Furthermore, as shown in FIG. 37, when the distal-side switch 5a and the proximal-side switch 5b are turned on, both of the contacts 85a and 85b are turned on.

Note that, though not shown, also the switch 86 is provided with contacts corresponding to the left-side switch 5c and the right-side switch 5d, respectively, and works similarly with the switch 85.

Each of the switches 5a to 5d instructs the changeover of the conduit direction in the first valve 70a and the second valve 70b and also the moving direction of the piston 70e inside of the syringe 70d.

Next description will be made on a method of inflating and contracting the balloon interlockingly with the balloon opposed thereto by using the syringe 70d thus configured.

First, as described above, the insertion portion 12 is pushed into the duodenum 90 until the objective lens 34 disposed in the distal end portion 17 of the insertion portion 12 captures the image of the papilla 95 and the papilla 95 is displayed on the monitor screen 4g of the monitor 4.

After that, when fixing the insertion portion 12 to the duodenum 90, the distal-side switch 5a and the proximal-side switch 5b of the switch 85 are depressed by the operator as shown in FIG. 37, and furthermore, the left-side switch 5c and the right-side switch 5d of the switch 86 are depressed.

As a result, as shown in FIG. 30, the air valve 70c is opened, and thereby the first valve 70a is changed over such that air is fed only to the balloon conduit 11f and the second valve 70b is changed over such that air is fed only to the balloon conduit 11h. Note that the piston 70e is located approximately the center between the one end side and the other end side in the syringe 70d at this time, as shown in FIG. 24.

After that, when air is supplied from the air feeding/sucking device 71, the air is introduced from the introducing port 70s into the syringe 70d. Then the air is fed from the supply port 70t to the balloon conduit 11f by the first valve 70a, and thereafter fed divergingly to the conduit 11fb and to the conduit 11fd, and also the air is fed from the supply port 70u to the balloon conduit 11h by the valve 70b, and thereafter divergingly fed to the conduit 11ha and to the conduit 11hc.

As a result, as shown in FIG. 31, the first balloon 10a to the fourth balloon 10d are inflated by pressurization to contact the intestinal wall of the duodenum 90, thereby fixing the insertion portion 12 to the duodenum 90 with the objective lens 34 capturing the papilla 95.

Subsequently, as shown in FIGS. 8 to 12, when the one-side surface 17k of the distal end portion 17 is brought close to the papilla 95 while maintaining the field of view direction S of the objective lens 34 unchanged, the input of each of the switches 5a to 5d is released, and thereafter the distal-side switch 5a is turned on, and proximal-side switch 5b is turned off, as shown in FIG. 36.

As a result, as shown in FIG. 32, the air valve 70c is closed and the piston 70e is moved in the syringe 70d to the other end side, that is, the supply port 70u side.

After that, air is sucked from the second balloon 10b and the fourth balloon 10d by depressurization, and the sucked air is fed to the first balloon 10a and the third balloon 10c via the balloon conduit 11f, the supply port 70t, the inside of the syringe 70d, the supply port 70u, and the balloon conduit 11h.

Note that, since the air valve 70c is closed at this time, the amount of air sucked from the second balloon 10b and the fourth balloon 10d and the amount of air fed to the first balloon 10a and the third balloon 10c are the same.

Accordingly, the first balloon 10a and the third balloon 10c are inflated by pressurization interlockingly with the second balloon 10b and the fourth balloon 10d being contracted.

Therefore, as described above, the one-side surface 17k of the distal end portion 17 is smoothly moved in parallel with respect to the field of view direction S toward the direction close to the papilla 95, which is the diameter direction of the distal end portion 17, parallel to the field of view direction S of the objective lens 34, and thereafter the catheter 60 projected from the channel aperture portion 27 is inserted into the bile duct 96 via the papilla 95.

Note that, in this case, the one-side surface 17k of the distal end portion 17 is brought close to the papilla 95 by using four balloons, that is, the first balloon 10a to the fourth balloon 10d, thereby enabling the one-side surface 17k of the distal end portion 17 to move in parallel more smoothly and stably than in the case shown in FIG. 26 where the first balloon 10a and the second balloon 10b are used.

Next, description will be made on the case where the insertion portion 12 of the endoscope 1 is inserted into the duodenum 90 by push-in operation of the insertion portion 12 by the operator to reach in the vicinity of the papilla 95, and thereafter, as described above, the distal end portion 17 of the insertion portion 12 is displayed deviated to the left side with respect to the papilla 95 on the screen 4g.

First, the insertion portion 12 of the endoscope 1 is inserted by the operator into the duodenum 90 by push-in operation of the insertion portion 12. After the insertion portion 12 reaches in the vicinity of the papilla 95, the operator projects the distal end of the catheter 60 from the channel aperture portion 27 and also adjusts the bending angle of the bending portion 16 so as to coincide the projecting direction K which is the insertion direction of the catheter 60 with the direction D of the bile duct 96. After that, the bending angle of the bending portion 16 is fixed by the operator.

Then, as shown in FIG. 31, the distal-side switch 5a and the proximal-side switch 5b of the switch 85 and the left-side switch 5c and the right-side switch 5d of the switch 86 are turned on, and thereby, as described above, the first balloon 10a to the fourth balloon 10d are inflated by pressurization, and the first balloon 10a to the fourth balloon 10d contact the intestinal wall of the duodenum 90. As a result, the insertion portion 12 is fixed to the duodenum 90 with the objective lens 34 capturing the papilla 95.

Next, after the input of each of the switches 5a to 5d is released, the left-side switch 5c of the switch 86 is turned on and the right-side switch 5d is turned off, thereby, as shown in FIG. 33, causing the air valve 70c to close and the piston 70e is moved in the syringe 70d to the other end side, that is, to the supply port 70u side.

Then, the first valve 70a is changed over such that air is fed only to the balloon conduit 11e, and furthermore, the second valve 70b is changed over such that air is fed only to the balloon conduit 11g.

As a result, air is sucked by depressurization from the first balloon 10a and the fourth balloon 10d on the right side, and the sucked air is fed to the second balloon 10b and the third balloon 10c on the left side via the balloon conduit 11e, the supply port 70t, the inside of the syringe 70d, the supply port 70u, and the balloon conduit 11g.

Note that, since the air valve 70c is closed at this time, the amount of air sucked from the first balloon 10a and the fourth balloon 10d and the amount of air fed to the second balloon 10b and the third balloon 10c are the same.

Accordingly, the second balloon 10b and the third balloon 10c are inflated by pressurization interlockingly with the first balloon 10a and the fourth balloon 10d being contracted.

As a result, the one-side surface 17k of the distal end portion 17 is smoothly moved in parallel with respect to the field of view direction S toward the right direction with respect to the papilla 95, which is the diameter direction of the distal end portion 17, parallel to the field of direction S of the objective lens 34.

Note that, when the one-side surface 17k of the distal end portion 17 is moved in parallel in the left direction, similarly air has only to be moved by the piston 70e such that the first balloon 10a and the fourth balloon 10d are inflated by pressurization and the second balloon 10b and the third balloon 10c are contracted by depressurization.

With the above-described configuration, the one-side surface 17k of the distal end portion 17 can be brought close to the papilla 95 or moved in left/right direction with respect to the papilla 95 by using four balloons, i.e., the first balloon 10a to the fourth balloon 10d.

Therefore, the one-side surface 17k of the distal end portion 17 can be moved in parallel more smoothly and stably than in the case shown in FIGS. 26, 29 where the two balloons are used. In addition, the configuration prevents the distal end portion 17 from rotating in a circumferential direction with the movement of the one-side surface more effectively than in the case shown in FIGS. 26, 29 where two balloons are used.

Note that another modified example is shown below.

Figure 38:
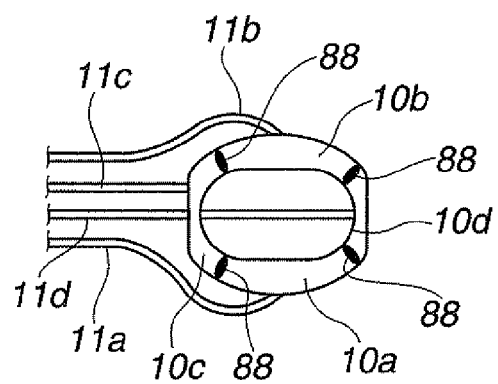
FIG. 38 is a view showing a modified example in which the balloons of FIG. 1 are configured separately from the endoscope.
Figure 39:
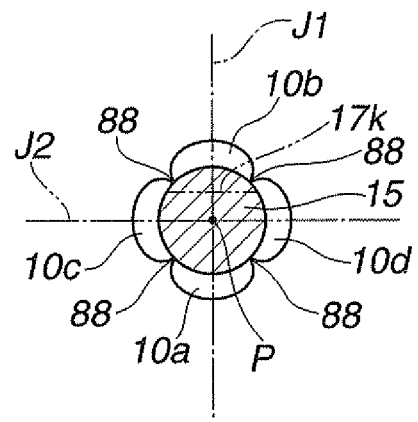
FIG. 39 is a cross-sectional view showing a state where the separately formed balloons of FIG. 38 are disposed at the distal end portion of the flexible tube portion of the endoscope insertion portion.

FIG. 38 is a view showing a modified example in which the balloons of FIG. 1 are configured separately from the endoscope, and FIG. 39 is a cross-sectional view showing a state where the separately formed balloons of FIG. 38 are disposed at the distal end portion of the flexible tube portion of the endoscope insertion portion.

In the above-described embodiment, the balloons 10a to 10d are integrally disposed at the above-described position on the outer circumference of the distal end portion 15s of the flexible tube portion 15, and the balloon conduits 11a to 11d communicated with the balloons 10a to 10d, respectively, are disposed inside of the insertion portion 12, as shown in FIGS. 3, 4.

The configuration is not limited to the above, as shown in FIG. 38, each of the balloons 10a to 10d may be formed separately from the endoscope insertion portion 12. In this case, the balloons 10a to 10d are formed by dividing one circular balloon by four seals 88 and the like, and the balloons 10a to 10d are respectively connected with the balloon conduits 11a to 11d communicated with the balloons 10a to 10d, respectively. In addition, the circular balloon including each of the balloons 10a to 10d is attachable/detachable with respect to the outer circumference of the flexible tube portion 15.

After the insertion portion 12 is inserted into the circular balloon thus configured, as shown in FIG. 39, each of the balloons 10a to 10d is disposed at the above-described predetermined position on the outer circumference of the distal end portion 15s of the flexible tube portion 15. Note that each of the balloon conduits 11a to 11d is located on the outer circumference of the insertion portion 12 in this case.

Note that yet another modified example is shown below.

Figure 40:
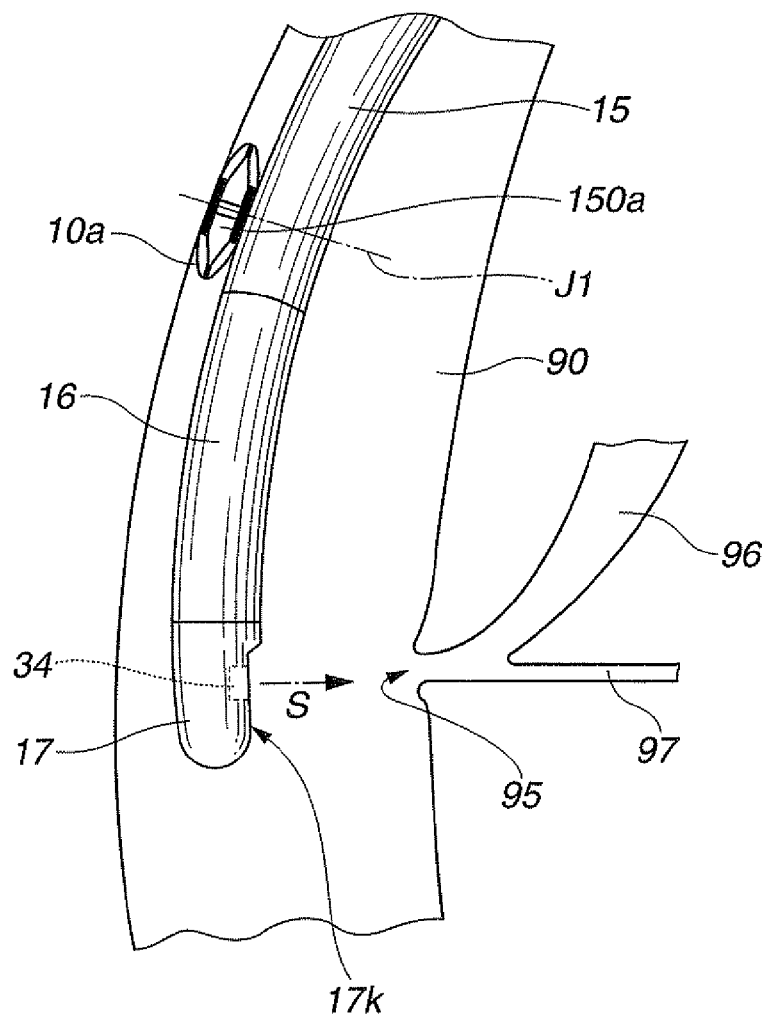
FIG. 40 is a view showing a modified example in which the mechanically inflated and contracted balloon is disposed on the outer circumferential surface of the distal end portion of the flexible tube portion so as to be located on an opposite direction side of the field of view direction of the objective lens.
Figure 41:
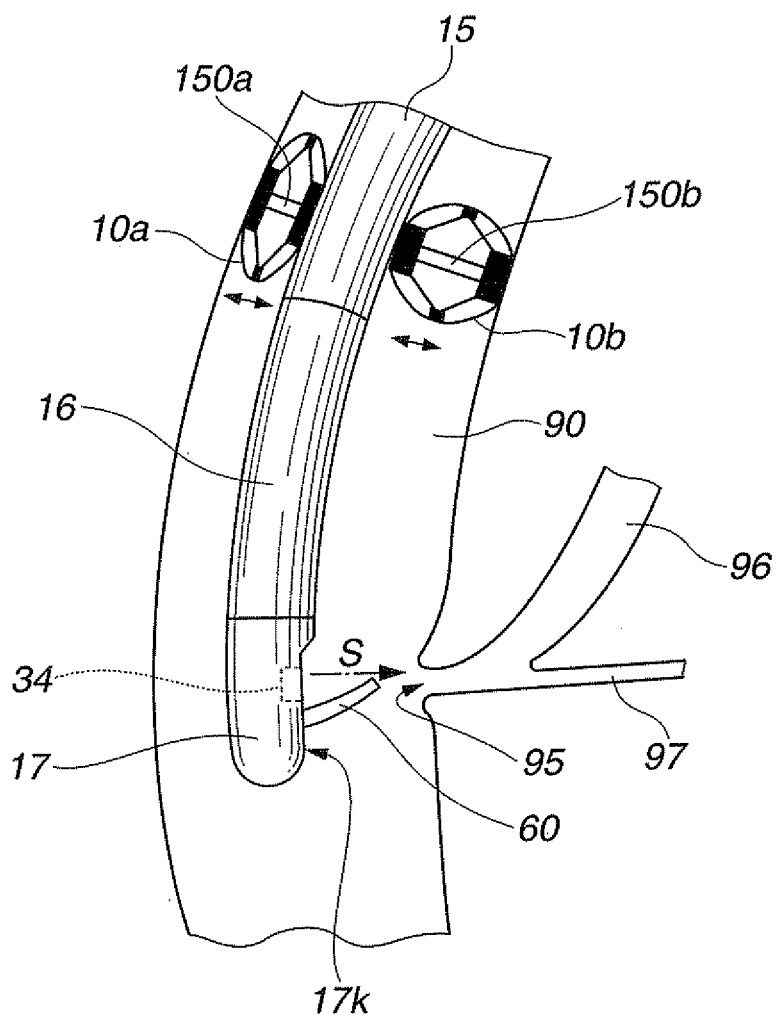
FIG. 41 is a view showing a modified example in which the balloon of FIG. 40 is disposed on the outer circumferential surface of the distal end portion of the flexible tube portion, both on the opposite direction side of the field of view direction of the objective lens and the field of view direction side of the objective lens.

FIG. 40 is a view showing a modified example in which the mechanically inflated and contracted balloon is disposed on the outer circumferential surface of the distal end portion of the flexible tube portion so as to be located on an opposite direction side of the field of view direction of the objective lens, and FIG. 41 is a view showing a modified example in which the balloon of FIG. 40 is disposed on the outer circumferential surface of the distal end portion of the flexible tube portion, both on the opposite direction side of the field of view direction of the objective lens and the field of view direction side of the objective lens.

The present embodiment shows that each of the balloons 10a to 10d is inflated and contracted by pressurization by sending air, depressurization by sucking air, or release of air. However, the configuration is not limited to the above, and each of the balloons 10a to 10d may be inflated and contracted by a mechanical configuration.

Specifically, as shown in FIG. 40, an expansion/contraction member 150a is disposed inside of the first balloon 10a. The expansion/contraction member 150a has such a configuration as electrically, for example by oil pressure, or fluidically, for example by water pressure, expandable/contractable with respect to the first axis J1.

When the first balloon 10a provided inside with the expansion/contraction member 150a thus configured is disposed, for example, on the outer circumferential surface of the distal end portion 15s of the flexible tube portion 15 so as to be located at a position on the first axis J1, which is on the opposite direction side of the field of view direction S of the objective lens 34, as shown in FIG. 40, after the field of direction S with respect to the papilla 95 is fixed, the first balloon 10a is expanded by expanding the expansion/contraction member 150a, thereby moving the one-side surface 17k of the distal end portion 17 in parallel in the diameter direction of the distal end portion 17 parallel to the field of view direction S, and bringing the one-side surface 17k close to the papilla 95, as described above.

Moreover, in addition to the balloon disposed on the opposite direction side of the field of view direction S, as shown in FIG. 41, the second balloon 10b including an expansion/contraction member 150b may be disposed on the outer circumferential surface of the distal end portion 15s of the flexible tube portion 15 so as to be located at a position on the first axis J1, which is on the field of view direction side S of the objective lens 34.

In this case, after the field of view direction S with respect to the papilla 95 is fixed, the expansion/contraction member 150a is expanded to inflate the first balloon 10a and the expansion/contraction member 150b is contracted to contract the second balloon 10b.

Accordingly, compared with the case where only one balloon, that is, the first balloon 10a including the expansion/contraction member 150a is used, the one-side surface 17k of the distal end portion 17 can be more smoothly and stably moved in parallel with respect to the papilla 95 in the diameter direction of the distal end portion 17 parallel to the field of view direction S, to be brought close to the papilla 95 as described above.

Note that, even in this case, the inflation of the first balloon 10a and the contraction of the second balloon 10b may be performed interlockingly with each other. In addition, in order to move in parallel the one-side surface 17k of the distal end portion 17 to left and right with respect to the papilla 95, the balloons including the expansion/contraction members inside may be disposed on the outer circumferential surface of the distal end portion 15s of the flexible tube portion 15 so as to be located at positions on the second axis J2, which are on the left and right sides with respect to the papilla 95.

If the first balloon 10a and the second balloon 10b are thus mechanically inflated and contracted, the expansion/contraction direction of the first balloon 10a and the second balloon 10b can be uniquely defined in comparison with the case where the first balloon 10a and the second balloon 10b are inflated and contracted by air. Therefore, the one-side surface 17k of the distal end portion 17 can be accurately moved in parallel with respect to the field of view direction S while securing the field of view with respect to the papilla 95.

(Second Embodiment)

Figure 42:
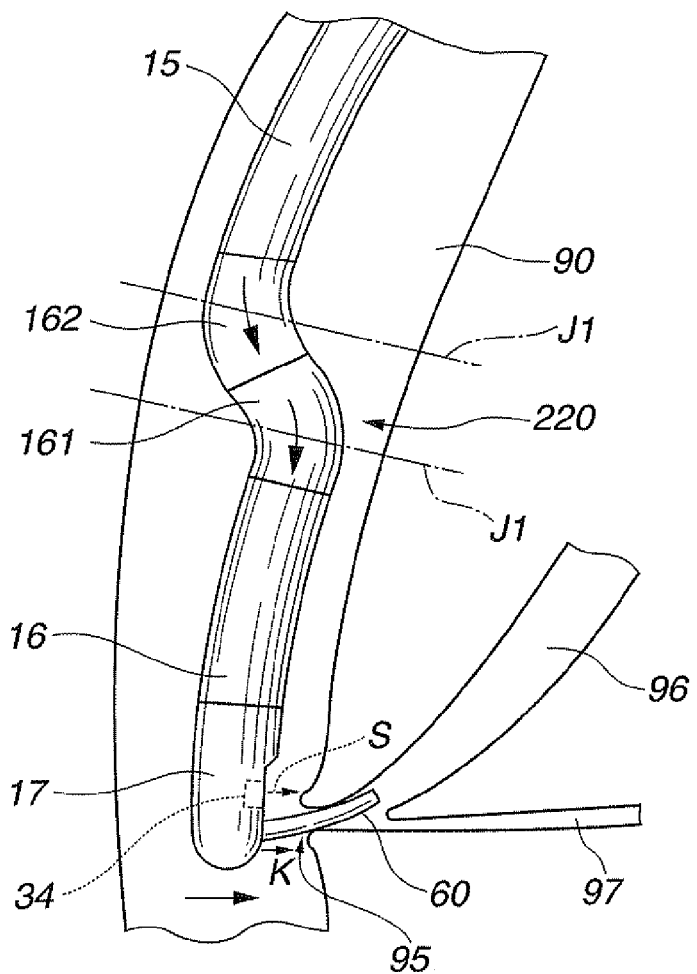
FIG. 42 is a view showing a state where a distal end side of an endoscope insertion portion of an endoscope system showing a second embodiment of the present invention is inserted into a body cavity.

FIG. 42 is a view showing a state where the distal end side of the endoscope insertion portion of the endoscope system showing a second embodiment of the present invention is inserted into a body cavity.

In comparison with the configuration of the endoscope insertion portion of the first embodiment, the configuration of the endoscope insertion portion of the present embodiment is different in that no balloon is provided on the outer circumference of the distal end portion of the flexible tube portion and three bending portions are provided in a linked manner between the flexible tube portion and the distal end portion. Therefore, only the different point will be described. The same components as those in the first embodiment are attached with the same reference numerals, and description thereof will be omitted.

As shown in FIG. 42, an endoscope insertion portion 220 of the present embodiment includes a distal end portion 17, a first bending portion 16, a second bending portion 161 as a moving mechanism, and a third bending portion 162 as a moving mechanism, and a flexible tube portion 15.

The first bending portion 16 is provided in a linked manner on the proximal end side in the insertion direction of the distal end portion 17, and operated to be bent for example in four directions by a bending operation knob 35 provided to the operation portion 13. The first bending portion 16 is the same as one in the above-described first embodiment.

The second bending portion 161 is provided in a linked manner on the proximal end side in the insertion direction of the first bending portion 16, and operated to be bent for example in four directions by a second bending operation knob, not shown, provided to the operation portion 13.

The third bending portion 162 is provided in a linked manner on the proximal end side in the insertion direction of the second bending portion 161 and operated to be bent for example in four directions by the third bending operation knob, not shown, provided to the operation portion 13.

The flexible tube portion 15 has flexibility, and includes the distal end portion 15s provided in a linked manner on the proximal end side in the insertion direction of the third bending portion 162.

Next, working of the present embodiment thus configured will be described.

First, as described above, the insertion portion 12 is pushed in by the operator until the objective lens 34 disposed in the distal end portion 17 of the insertion portion 12 captures the image of the papilla 95 and the papilla 95 is displayed on the monitor screen 4g of the monitor 4, and also the first bending portion 16 is bent by the operator operating the bending operation knob 35.

Next, from the channel aperture portion 27 of the distal end portion 17 is projected by the operator the distal end side of the catheter 60 inserted into the treatment instrument insertion channel from the aperture 40a of the treatment instrument insertion port 40, and then the bending angle of the bending portion 16 is fixed. As a result, the projecting direction K which is the insertion direction of the catheter 60 projected from the channel aperture portion 27 is fixed. Note that the projecting direction K is fixed so as to coincide with the field of view direction S of the objective lens 34 at this time.

In this state, as shown in FIG. 42, by the operator operating the third bending operation knob, the third bending portion 162 is bent, on the first axis J1, to the side of the field of view direction S of the objective lens 34, specifically to the papilla 95 side, and by operating the second bending operation knob, the second bending portion 161 is bent, on the first axis J1, to the opposite direction side of the field of view direction S of the objective lens 34, specifically to the opposite side of the papilla 95 by the same bending amount as that of the third bending portion 162.

As a result, the one-side surface 17k of the distal end portion 17 is moved in parallel with respect to the field of view direction S toward the direction close to the papilla 95, which is the diameter direction of the distal end portion 17, parallel to the field of view direction S of the objective lens 34. After that, the distal end portion side of the catheter 60 projected from the channel aperture portion 27 is inserted into the bile duct 96.

Note that, when the one-side surface 17k of the distal end portion 17 is brought close to the papilla 95, the field of view direction S of the objective lens 34 or the insertion direction K of the catheter 60 before the movement and the field of view direction S of the objective lens 34 or the insertion direction K of the catheter 60 after the movement are the same.

Therefore, unlike the conventional configuration in which the one-side surface 17k is brought close to the papilla 95 by bending only the first bending portion 16, the distal end of the catheter 60 does not deviate in up/down direction with respect to the papilla 95 before and after the movement. That is, the one-side surface 17k is brought close to the papilla 95 while maintaining the field of view direction S and the insertion direction K, thereby facilitating the insertion of the catheter 60 into the bile duct 96.

Note that, when the operator would like to move the one-side surface 17k in parallel to the field of view direction S toward the left direction with respect to the papilla, the operator bends the third bending portion 162 to the left side with respect to the field of view direction S on the second axis J2 by operating the third bending operation knob, though not shown, and also bends the second bending portion 161 to the right side with respect to the field of view direction S on the second axis 12 by operating the second bending operation knob, by the same bending amount as that of the third bending portion 162.

Furthermore, when the operator would like to move the one-side surface 17k in parallel to the field of view direction S toward the right direction with respect to the papilla 95, the operator bends the third bending portion 162 to the right side with respect to the field of view direction S on the second axis J2 by operating the third bending operation knob, though not shown, and also bends the second bending portion 161 to the left side with respect to the field of view direction S on the second axis J2 by operating the second bending operation knob, by the same bending amount as that of the third bending portion 162.

Thus, the present embodiment shows that the one-side surface 17k of the distal end portion 17 is moved in parallel with respect to the papilla 95 in the diameter direction of the distal end portion 17 parallel to the field of view direction S of the objective lens 34, by bending the second bending portion 161 and the third bending portion 162 in the directions opposite to each other.

With this configuration, there is no need to use the balloons 10 and the like, the production cost is reduced in comparison with the above-described first embodiment. In addition, the one-side surface 17k can be moved in parallel only by operating the insertion portion 12, thereby improving the operability.

In addition, the second bending portion 161 and the third bending portion 162 are disposed separately from the first bending portion 16, so that fine tuning by bending operation of the first bending portion 16 can be performed after bending the second bending portion 161 and the third bending portion 162.

(Third Embodiment)

Figure 43:
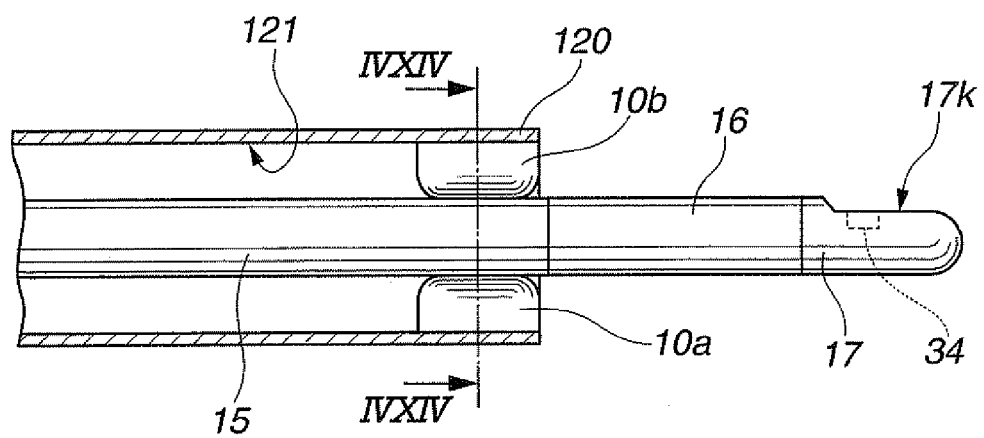
FIG. 43 is a view showing a state where the distal end side of the endoscope insertion portion of the endoscope system showing a third embodiment of the present invention is covered with a cylindrical member.
Figure 44:
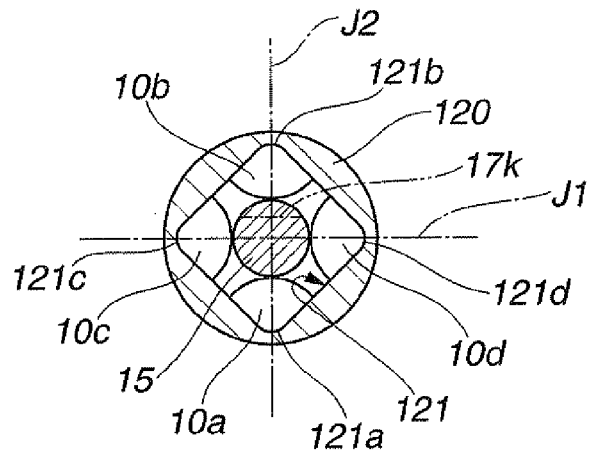
FIG. 44 is a cross-sectional view along with the IVXIV-IVXIV line of FIG. 43.

FIG. 43 is a view showing a state where the distal end side of the endoscope insertion portion of the endoscope system showing a third embodiment of the present invention is covered with a cylindrical member, FIG. 44 is a cross-sectional view along with the IVXIV-IVXIV line of FIG. 43.

Figure 45:
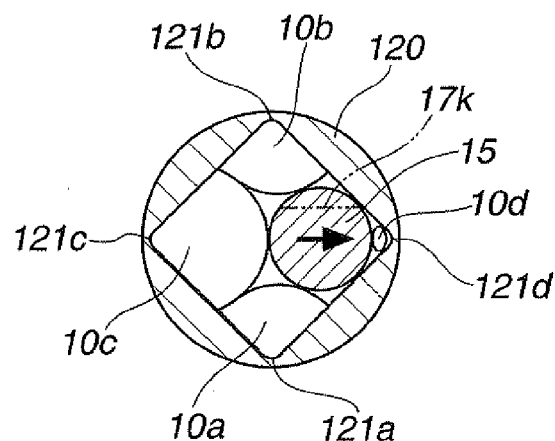
FIG. 45 is a cross-sectional view showing an example in which a one-side surface of the distal end portion of FIG. 43 is moved in parallel to the field of view direction toward the right side with respect to the papilla.
Figure 46:
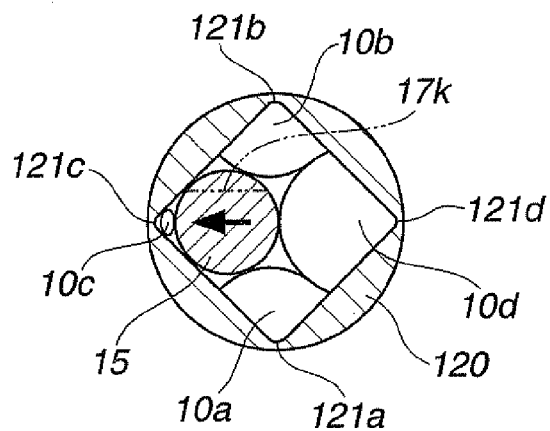
FIG. 46 is a cross-sectional view showing an example in which the one-side surface of the distal end portion of FIG. 43 is moved in parallel to the field of view direction toward the left side with respect to the papilla.
Figure 47:
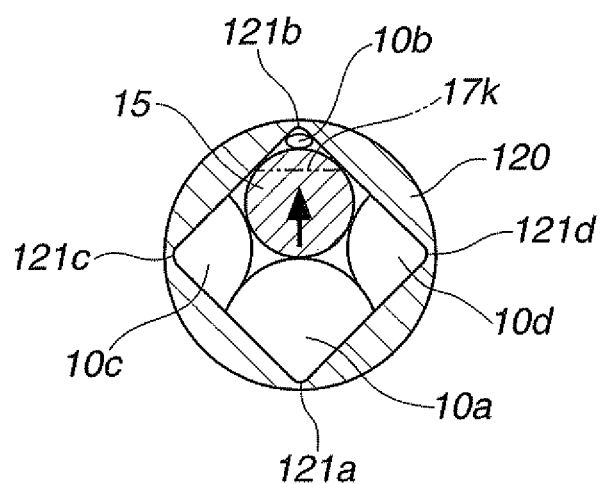
FIG. 47 is a cross-sectional view showing an example in which the one-side surface of the distal end portion of FIG. 43 is moved in parallel to the field of view direction toward the proximal side with respect to the papilla.
Figure 48:
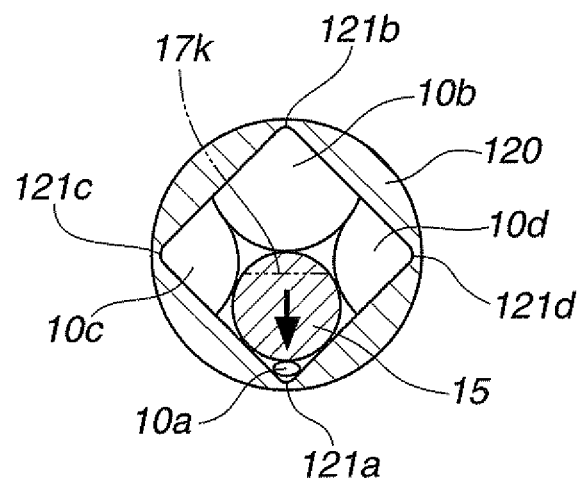
FIG. 48 is a cross-sectional view showing an example in which the one-side surface of the distal end portion of FIG. 43 is moved in parallel to the field of view direction toward the distal side with respect to the papilla.

Furthermore, FIG. 45 is a cross-sectional view showing an example in which the one-side surface of the distal end portion of FIG. 43 is moved in parallel to the field of view direction toward the right side with respect to the papilla, FIG. 46 is a cross-sectional view showing an example in which the one-side surface of the distal end portion of FIG. 43 is moved in parallel to the field of view direction toward the left side with respect to the papilla, FIG. 47 is a cross-sectional view showing an example in which the one-side surface of the distal end portion of FIG. 43 is moved in parallel to the field of view direction toward the side close to the papilla, and FIG. 48 is a cross-sectional view showing an example in which the one-side surface of the distal end portion of FIG. 43 is moved in parallel to the field of view direction toward the side away from the papilla.

The configuration of the endoscope system of the present embodiment is different from that of the endoscope system in the first embodiment only in that a balloon is disposed on the cylindrical member covering the endoscope insertion portion (hereinafter called overtube). Therefore, only the different point will be described. The same components as those in the first embodiment are attached with the same reference numerals, and description thereof will be omitted.

As shown in FIGS. 43, 44, an overtube 120 having predetermined thickness and rigidity can cover the outer circumference of the insertion portion 12 of the endoscope 1, more specifically, the outer circumference of the flexible tube portion 15. Note that the outer diameter of the overtube 120 is formed to be slightly smaller than that of the duodenum 90.

As shown in FIG. 44, an inner circumferential surface 121 of the overtube 120 has a rectangular shape and includes corner portions 121a to 121d forming the rectangular shape, which are positioned on the first axis J1 or the second axis J2. Into each of the corner portions 121a to 121d is integrally fitted each of the above-described four balloons 10a to 10d inflatable and contractable in the inner circumferential direction of the overtube by feeding and sucking of air, for example.

Note that the four balloons 10a to 10d may be formed separately from the respective corner portions 121a to 121d and attachable to/detachable from the endoscope 1 or the overtube 120.

As a result, on the inner circumferential surface 121, the first balloon 10a is disposed on the second axis J2 so as to oppose to the second balloon 10b, and the third balloon 10c is disposed on the first axis J1 so as to oppose to the fourth balloon 10d.

Next, the mounting position of each of the balloons 10a to 10d with respect to the overtube 120 is described with reference to FIGS. 49 and 50.

Figure 49:
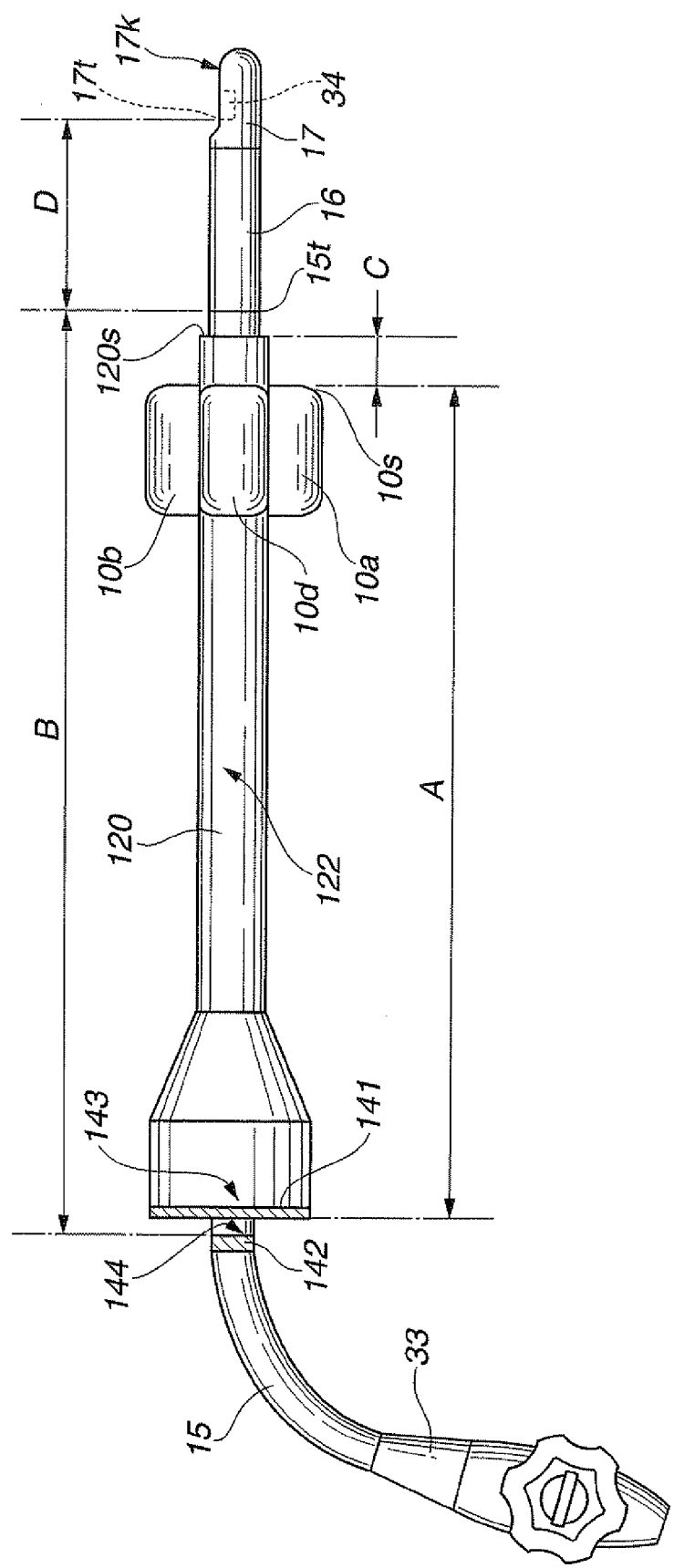
FIG. 49 is a view showing an example in which balloons are provided on an outer circumference of an overtube covering the endoscope insertion portion of FIG. 43 and indicators are provided on a proximal end side of the insertion direction of the endoscope insertion portion and the overtube.
Figure 50:
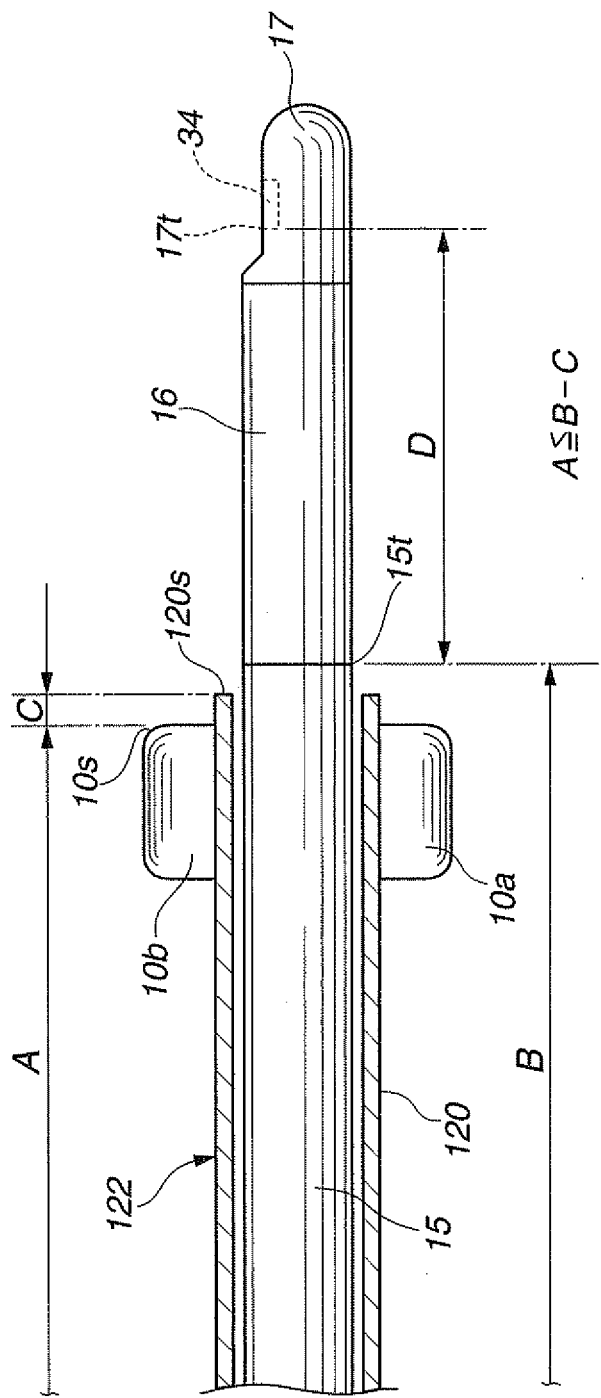
FIG. 50 is a view showing the mounting positions of the balloons from the distal end of the overtube with respect to the outer circumference of the overtube in a case where the overtube of FIG. 49 is rigid.
Figure 51:
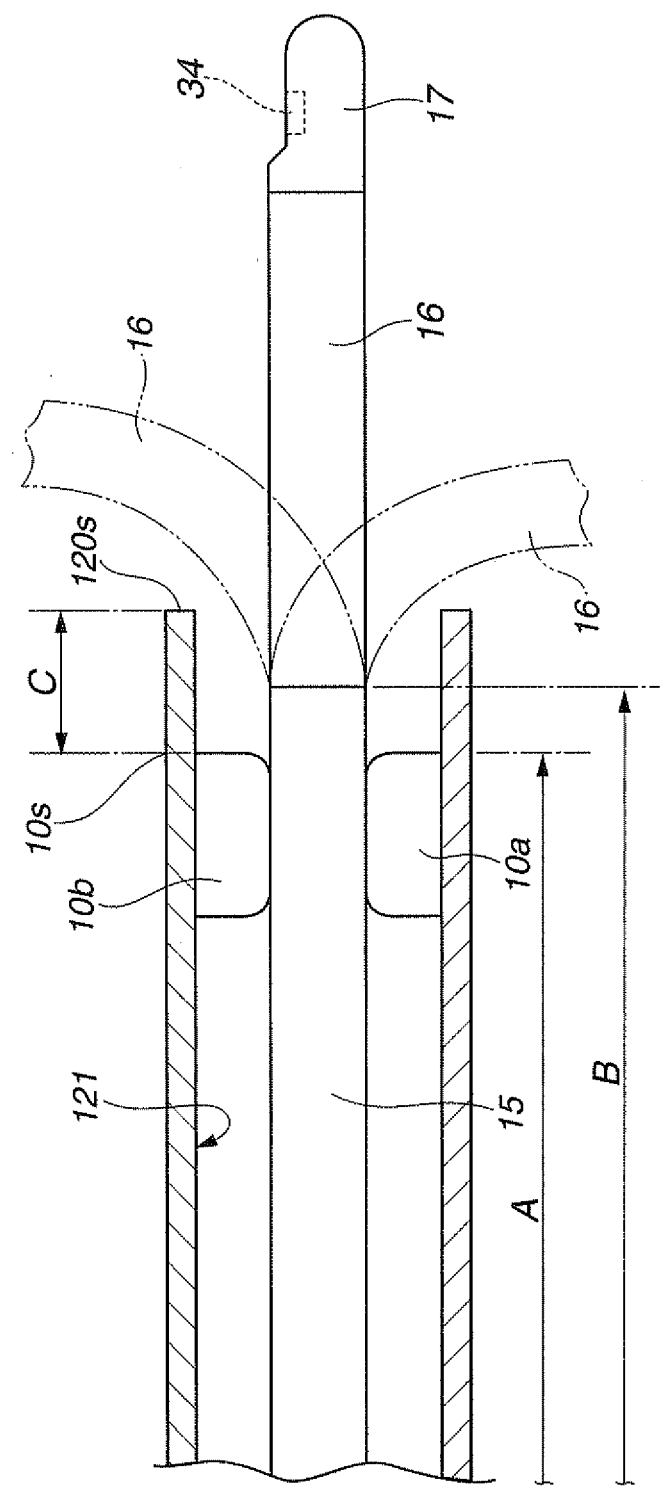
FIG. 51 is a view showing the mounting positions of the balloons from the distal end of the overtube with respect to the inner circumference of the overtube in a case where the overtube of FIG. 49 is rigid.

FIG. 49 is a view showing an example in which balloons are provided on an outer circumference of the overtube covering the endoscope insertion portion of FIG. 43 and indicators are provided on the proximal end side of insertion direction of the endoscope insertion portion and the overtube, FIG. 50 is a view showing the mounting position of the balloon from the distal end of the overtube with respect to the outer circumference of the overtube in a case where the overtube of FIG. 49 is rigid, and FIG. 51 is a view showing the mounting positions of the balloons from the distal end of the overtube with respect to the inner circumference of the overtube in a case where the overtube of FIG. 49 is rigid.

Figure 52:
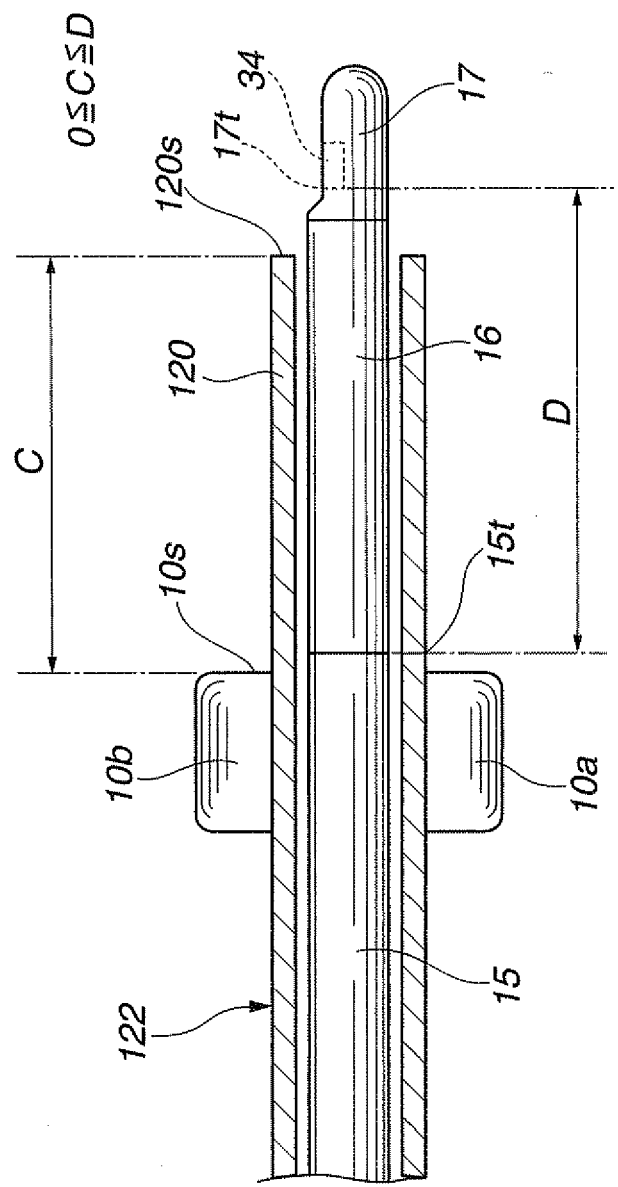
FIG. 52 is a view showing the mounting positions of the balloons from the distal end of the overtube with respect to the outer circumference of the overtube in a case where the overtube of FIG. 49 is flexible.
Figure 53:
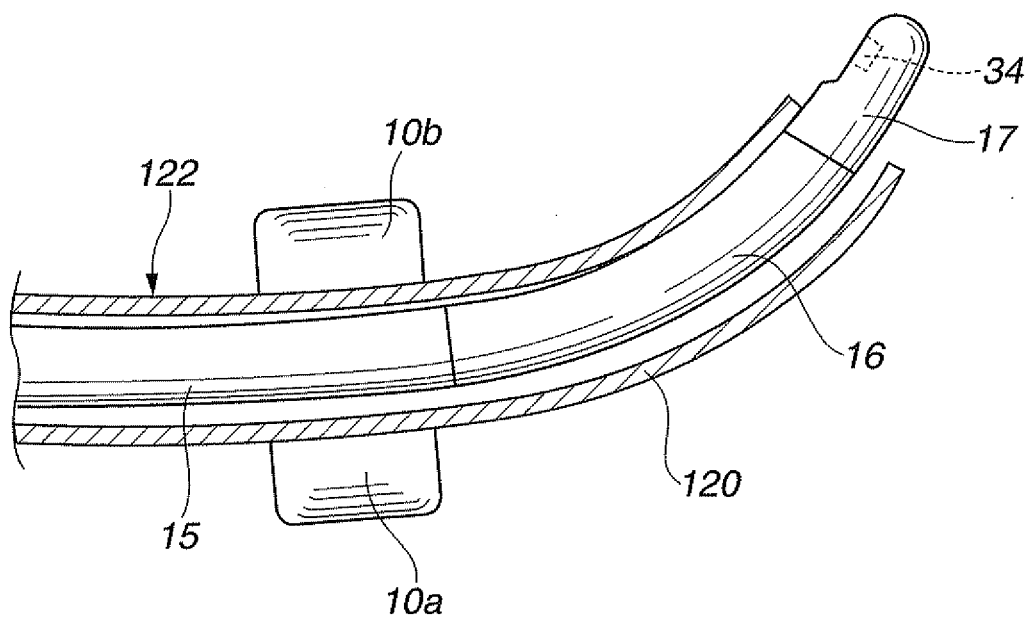
FIG. 53 is a view showing a state where the bending portion is bent with the overtube placed thereover.
Figure 54:
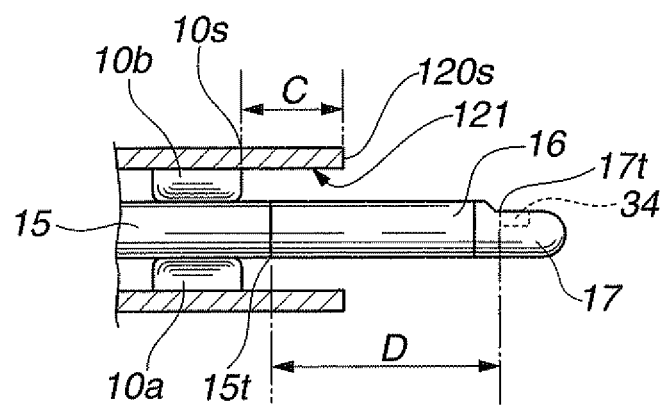
FIG. 54 is a view showing the mounting positions of the balloons from the distal end of the overtube with respect to the inner circumference of the overtube in a case where the overtube of FIG. 49 is flexible.

Furthermore, FIG. 52 is a view showing the mounting positions of the balloons from the distal end of the overtube with respect to the outer circumference of the overtube in a case where the overtube of FIG. 49 is flexible, FIG. 53 is a view showing a state where the bending portion is bent with the overtube placed thereover, and FIG. 54 is a view showing the mounting positions of the balloons from the distal end of the overtube with respect to the inner circumference of the overtube in a case where the overtube of FIG. 49 is flexible.

As shown in FIG. 49, each of the balloons 10a to 10d may be fixed onto the outer circumferential surface 122 of the overtube 120. Note that each of the balloons 10a to 10d may be configured separately with respect to the outer circumferential surface 122 of the overtube 120 and attachable thereto/detachable therefrom. In addition, in this case, the diameter of the inner circumferential surface 121 of the overtube 120 is formed to be slightly larger than that of the outer circumference of the endoscope insertion portion 12.

In addition, each of the balloons 10a to 10d provided on the outer circumference of the insertion portion 12 is disposed such that a contact point (hereinafter called proximal point) 10s of the distal end in the insertion direction into the duodenum 90 is located at the position on the side nearer to the proximal end by a first distance C from the distal end 120s of the overtube 120.

Note that, also in the case where each of the balloons 10a to 10d is provided on the inner circumferential surface 121 of the overtube 120, similarly, each of the balloons 10a to 10d is disposed such that the proximal point 10s with respect to the outer circumferential of the distal end portion 15s of the flexible tube portion 15 is located at the position on the side nearer to the proximal end by the first distance C from the distal end 120s of the overtube 120.

In addition, a first indicator 141 is formed at the proximal end of the overtube 120 which is located on the side nearer to the proximal end by a second distance A from the proximal point of each of the balloons 10a to 10d. Furthermore, a third indicator 143 for adjusting a position in a rotational direction is formed in the vicinity of the first indicator 141.

In addition, also in the endoscope insertion portion 12, a second indicator 142 is formed at the position on the side nearer to the proximal end by a fourth distance B from the distal end 15t of the distal end portion 15s of the flexible tube portion 15. Furthermore, a fourth indicator 144 for adjusting a position in the rotational direction is formed in the vicinity of the second indicator 142.

Note that, though not shown, the first indicator 141 and the second indicator 142 may be a first engaging portion and a second engaging portion for engaging the overtube 120 with the insertion portion 12, respectively.

Furthermore, hereinafter, the distal end 15t of the flexible tube portion 15 is assumed to be located on the side nearer to the proximal end by a fifth distance D from the proximal end 17t in the insertion direction of the objective lens 34 of the distal end portion 17 of the insertion portion 12.

Here, in either case where each of the balloons 10a to 10d is disposed on the inner circumferential surface 121 or on the outer circumferential surface 122 of the overtube 120, when the overtube 120 is rigid and the clearance between the outer circumference of the insertion portion 12 and the overtube 120 is small, if the endoscope insertion portion 12 is covered with the overtube 120 and the overtube 120 is inserted into the distal end side of the insertion portion 12, and then the bending portion 16 of the insertion portion 12 is covered with the overtube 120, the bending operation of the bending portion 16 becomes impossible.

Therefore, when in use, the distal end 120s of the overtube 120 needs to be surely located nearer to the proximal end side than the distal end 15t of the flexible tube portion 15. In addition, each of the balloons 10a to 10d needs to be surely located at the same position as or at the position nearer to the proximal end side than the distal end 15t of the flexible tube portion 15.

Therefore, as shown in FIG. 50, if the second distance A is set to the value equal to or less than the value obtained by subtracting the first distance C from the fourth distance B ($A \leq B-C$), the bending portion 16 can be easily and surely projected from the distal end of the overtube 120 when the insertion portion 12 is covered with the overtube 120 and the first indicator 141 and the second indicator 142 formed on the insertion portion 12 are coincided with each other.

In addition, in this case, the first distance C is set to the value equal to or less than the value obtained by subtracting the second distance A from the fourth distance B ($C \leq B-A$). Accordingly, each of the balloons 10a to 10d is surely located at the same position as or the position nearer to the proximal end side than the position of the distal end 15t of the flexible tube portion 15.

Note that, as shown in FIG. 51, only in the case where each of the balloons 10a to 10d is disposed on the inner circumferential surface 121 of the overtube, and the clearance between the outer circumference of the insertion portion 12 and the overtube 120 is large, the first distance C may be set to a value larger than the value obtained by subtracting the second distance A from the fourth distance B ($C \geq B-A$), as long as the distance is within the range not interfering with the bending of the bending portion 16.

Next, in the case where the overtube 120 is flexible, and each of the balloons 10a to 10d is located on the outer circumferential surface 122 of the overtube, since the overtube 120 is bendable as the bending portion 16 is bent as shown in FIG. 53 even after the overtube 120 is placed over the endoscope insertion portion 12, the bending portion 16 of the endoscope insertion portion 12 may be covered with the overtube 120. However, each of the balloons 10a to 10d needs to be surely located at the same position as or the position nearer to the proximal end side than the position of the distal end 15t of the flexible tube portion 15.

Therefore, as shown in FIG. 52, if the second distance A is set to a value equal to or less than the value obtained by subtracting the first distance C from the fourth distance B ($A \leq B-C$) and then the first distance C is set to a value equal to or not less than 0 (zero) and equal to or not more than the fifth distance D ($0 \leq C \leq D$), each of the balloons 10a to 10d are surely located at the same position or the position nearer to the proximal end side than the position of the distal end 15t of the flexible tube portion 15.

Note that, this is the same as in the case where each of the balloons 10a to 10d is disposed on the inner circumferential surface 121 of the overtube 120, as shown in FIG. 54.

Next, the working of the present embodiment thus configured is described.

First, as described above, the insertion portion 12 is pushed in until the objective lens 34 disposed to the distal end portion 17 of the insertion portion 12 captures the image of the papilla 95 and the papilla 95 is displayed on the monitor screen 4g of the monitor 4, and the first bending portion 16 is bent by operating the bending operation knob 35.

Next, from the channel aperture portion 27 of the distal end portion 17 is projected by the operator the distal end side of the catheter 60 inserted into the treatment instrument insertion channel from the aperture 40a of the treatment instrument insertion port 40, and then the bending angle of the bending portion 16 is fixed.

This causes a projecting direction K, which is the insertion direction of the catheter 60 projected from the channel aperture portion 27, to be fixed. Note that the projecting direction K is fixed so as to coincide with the field of view direction S of the objective lens 34 at this time.

In this state, the overtube 120 is placed on the outer circumference of the endoscope insertion portion 12 from the proximal end side thereof, and the overtube 120 is inserted into the duodenum 90.

At this time, the overtube 120 is inserted until the indicator 142 formed on the insertion portion 12, which is not inserted into the body cavity, and the indicator 141 formed on the overtube 120, which is not inserted into the body cavity coincide with each other. As a result, each of the balloons 10a to 10d is surely located nearer to the proximal end side than the distal end 15t of the flexible tube portion 15, as described above.

After that, the overtube 120 is rotated with respect to the insertion portion 12 until the third indicator 143 formed on the overtube 120 coincides with the fourth indicator 144 formed on the insertion portion 12.

Accordingly, the third balloon 10c and the fourth balloon 10d are disposed on the outer circumferential surface of the distal end portion 15s of the flexible tube portion 15 so as to oppose to each other at line-symmetric positions with respect to the first axis J1, and the first balloon 10a and the second balloon 10b are disposed so as to oppose to each other at line-symmetric positions with respect to the second axis J2.

More specifically, when each of the balloons 10a to 10d is disposed on the inner circumferential surface 121 of the overtube 120, the second balloon 10b is disposed on the outer circumferential surface of the distal end portion 15s of the flexible tube portion 15 so as to be located at the position on the first axis J1, which is on the field of direction S side, in other words, on the side where the one-side surface 17k is formed, and the first balloon 10a is disposed at the position on the first axis J1, which is on the opposite direction side of the field of view direction S of the objective lens 34.

In addition, the third balloon 10c is disposed at the position on the second axis, which is on one end side, for example the left side, of the direction orthogonal to the field of view direction S of the objective lens 34 and the fourth balloon 10d is disposed at the position on the second axis, which is on the other end side, for example the right side of the direction orthogonal to the field of view direction S of the objective lens 34.

After that, the first balloon 10a to the fourth balloon 10d are inflated by feeding air with the method described above in the first embodiment, and thereby the distal end portion 15s of the flexible tube portion 15 is fixed onto the inner circumferential surface 121 of the overtube 120.

In this state, when the one-side surface 17k of the distal end portion 17 is moved in parallel to the field of view direction S toward the right side with respect to the papilla 95, as shown in FIG. 45, the third balloon 10c is inflated and the fourth balloon 10d is contracted.

In addition, when the one-side surface 17k of the distal end portion 17 is moved in parallel to the field of view direction S toward the left side with respect to the papilla 95, as shown in FIG. 46, the third balloon 10c is contracted and the fourth balloon 10d is inflated.

Moreover, when the one-side surface 17k of the distal end portion 17 is moved in parallel to the field of view direction toward the side close to the papilla 95, as shown in FIG. 47, the second balloon 10b is contracted and the first balloon 10a is inflated.

Moreover, when the one-side surface 17k of the distal end portion 17 is moved in parallel to the field of view direction S toward the side away from the papilla 95, as shown in FIG. 48, the second balloon 10b is inflated and the first balloon 10a is contracted.

Accordingly, the one-side surface 17k of the distal end portion 17 is moved in parallel to the field of view direction S toward the right side, the left side, the close side, and the distant side with respect to the papilla 95. As a result, it becomes easier to insert and extract the catheter 60 to and from the papilla 95.

Note that this is the same in the case where each of the balloons 10a to 10d is disposed on the outer circumferential surface 122 of the overtube 120.

Thus, in the present embodiment, the balloons 10a to 10d are respectively provided to the corner portions 121a to 121d located on the first axis J1 and the second axis J2 on the rectangular-shaped inner circumferential surface 121 of the overtube 120 covering the insertion portion 12 such that each two of the balloons are opposed to each other, respectively.

In the above described first embodiment in which each of the balloons 10a to 10d is inflated to fix the insertion portion 12 onto the inner wall of the duodenum 90, in a case where the inner wall of the duodenum 90 is flexible, the inner wall expands and contracts with respect to each of the inflated balloons 10a to 10d, so that fixing the insertion portion 12 onto the inner wall is sometimes difficult. In addition, when the one-side surface 17k is moved with respect to the papilla 95 in parallel to the field of view direction S, the moving direction is sometimes deviated from a desired direction.

However, in the present embodiment having the above-described configuration, when each of the balloons 10a to 10d is disposed on the inner circumferential surface 121 of the overtube 120, each of the balloons 10a to 10d is inflated in the overtube 120 having a predetermined rigidity to fix the insertion portion 12 onto the inner circumferential surface 121 of the overtube 120, thereby eliminating the influence of the softness of the inner wall of the duodenum 90 on the fixing of the insertion portion 12 and the moving of the one-side surface 17k.

That is, the insertion portion 12 can be surely fixed and the one-side surface 17k can be surely moved in a desired direction at the time of moving the one-side surface 17k with respect to the papilla 95 in parallel to the field of view direction S.

In addition, each of the balloons 10a to 10d is fixed to each of the corner portions 121a to 121d on the inner circumferential surface 121 of the overtube 120, thereby preventing the distal end portion 17 from rotating in the outer circumferential direction when moving the one-side surface 17k of the distal end portion 17 in association with the inflation and contraction of each of the balloons 10a to 10d.

Furthermore, if each of the balloons 10a to 10d is disposed on the outer circumferential surface 122 of the overtube 120, the diameters of the overtube 120 and the insertion portion 12 can be reduced.

Note that, the inner circumferential surface 121 of the overtube 120 is in a rectangular shape in the present embodiment, however there is no limitation placed thereon. The inner circumferential surface 121 may be formed in any shape as long as the one-side surface 17k of the distal end portion 17 can be stably moved in association with the inflation and contraction of the each of the balloons 10a to 10d.

In addition, the present embodiment can be applied to the case where each of the balloons 10a to 10d is located at a position shown in above-described FIGS. 30 to 33.

Furthermore, in the present embodiment, the insertion portion 12 is inserted into the duodenum 90 and the overtube 120 is placed on the outer circumference of the insertion portion 12 to be inserted into the duodenum 90, and thereafter the positions in the circumferential direction of the balloons 10a to 10d are adjusted by rotating the overtube 120 until the third indicator 143 and the fourth indicator 144 coincide with each other.

However, there is no limitation placed on the above, and each of the balloons 10a to 10d may be inflated before the overtube 120 is placed on the insertion portion 12, and the overtube 120 may be placed in a state where the position of each of the balloons 10a to 10d is adjusted with respect to the insertion portion 12.

Note that modified examples are shown below.

In the above-described first to the third embodiments, description was made taking the case where the endoscope is inserted in the duodenum 90 as an example, however, there is no limitation placed thereon. The present invention can be applied to the case where an endoscope or treatment instrument is inserted in a region to be inspected in a canaliculus in a body cavity.

In addition, description was made taking a side-view endoscope as an example of the endoscope, however, there is no limitation placed thereon. The present invention may be applied to a direct-view endoscope as long as the purpose is to move the distal end of the endoscope in a diameter direction with respect to an object to bring the distal end close to the object.

In addition, the endoscope was described taking the medical endoscope to be inserted into a body cavity as an example, however there is no limitation placed thereon. The present invention may be applied to an industrial endoscope to be inserted into a pipe and the like in a factory.

Furthermore, description was made taking the case where the balloons 10 are provided four in number to the endoscope insertion portion 12 or the overtube 120 so as to be line-symmetric with respect to the first axis J1 or the second axis J2 as an example. However, there is no limitation in the number of the balloons, and it is needless to say that the present invention can be applied even if the number of the balloons is one or two.

In addition, though the treatment instrument is shown taking the catheter as an example, it is needless to say that the present invention can be applied to the treatment instrument other than the catheter.

Note that, though the embodiments of the present invention have been described above, the present invention is not limited to the above-described embodiments, and various changes and modifications are possible without departing from the spirit of the present invention.

What is claimed is:

1. An endoscope system comprising:
a side-view endoscope including an elongated insertion portion, the elongated insertion portion including a bendable bending portion, a flexible tube portion having flexibility and provided on a proximal end side of the bendable bending portion, and a distal end portion provided on a distal end side of the bendable bending portion, wherein the elongated insertion portion is configured to be inserted into a lumen;
four balloons which are expandable and contractable in a diameter direction of the elongated insertion portion in accordance with air feeding and air sucking by an air feeding/sucking device and which are disposed on a distal end side of the flexible tube portion, the balloons moving a one-side surface provided in the distal end portion in parallel to the diameter direction of the elongated insertion portion, separately from bending of the bending portion, the one-side surface being located in a circumferential direction of the distal end portion along an insertion direction of the elongated insertion portion and being parallel to a central axis of the elongated insertion portion; and
an expansion/contraction mechanism provided in a linked manner to the four balloons and the air feeding/sucking device, and configured to expand and contract the four balloons,
wherein:
the four balloons are disposed in the circumferential direction on the distal end side of the flexible tube portion and include:
a third balloon and a fourth balloon provided opposed to each other at line-symmetric positions with respect to a first axis passing the central axis of the elongated insertion portion and parallel to a field of view direction of an objective lens provided on the one-side surface, and
a first balloon and a second balloon provided opposed to each other at line-symmetric positions with respect to a second axis passing the central axis of the elongated insertion portion and orthogonal to the first axis, and
the expansion/contraction mechanism includes:
a first balloon conduit having one end connected to the first balloon;
a second balloon conduit having one end connected to the second balloon;
a third balloon conduit having one end connected to the third balloon;
a fourth balloon conduit having one end connected to the fourth balloon; and
a syringe including:
an introducing port for introducing air from the air feeding/sucking device,
an introducing valve for changing over whether or not to introduce the air from the air feeding/sucking device into the introducing port,
a first supply port on one end side of the syringe and a first valve,
a second supply port on an other end side of the syringe and a second valve, and
a piston movable between the one end side and the other end side,
wherein, the first valve is connected with an other end of the first balloon conduit and an other end of the fourth balloon conduit, and the first valve changes over an air supply direction to supply the air inside the syringe to either the first balloon conduit or the fourth balloon conduit, and the second valve is connected with an other end of the second balloon conduit and an other end of the third balloon conduit, and the second valve changes over an air supply direction to supply the air in the syringe to either the second balloon conduit or the third balloon conduit,
wherein the balloons are configured such that:
in a state where the field of view direction of the objective lens and a protruding direction of a treatment instrument protruded from an aperture formed on the one-side surface coincide with each other by fixing a bending angle of the bendable bending portion, and in a state where the air supply direction is changed over to the first balloon conduit by the first valve, the air supply direction is changed over to the second balloon conduit by the second valve, the introducing valve is opened, and the piston is positioned in the syringe in the center between the one end side and the other end side of the syringe, when the air is supplied from the air feeding/sucking device to the first balloon and the second balloon via the introducing port, the syringe, the first supply port, the second supply port, the first balloon conduit, and the second balloon conduit, the first and second balloons expand in the diameter direction, and when the piston moves inside the syringe toward the one end side in a state where the introducing valve is closed, the air inside the second balloon is moved into the first balloon, via the second balloon conduit, the syringe, and the first balloon conduit, and thereby the second balloon contracts in the diameter direction and the first balloon expands in the diameter direction interlockingly with the contraction, thereby moving the one-side surface in parallel to a position close to a papilla with respect to the field of view direction of the objective lens by utilizing the expansion of the first balloon, while making the field of view direction of the objective lens and the protruding direction coincide with each other, and in a state where the field of view direction of the objective lens and the protruding direction of the treatment instrument protruded from the aperture formed on the one-side surface coincide with each other by fixing a bending angle of the bendable bending portion, and in a state where the air supply direction is changed over to the fourth balloon conduit by the first valve, the air supply direction is changed over to the third balloon conduit by the second valve, the introducing valve is opened, and the piston is positioned in the syringe in the center between the one end side and the other end side of the syringe, when the air is supplied from the air feeding/sucking device to the third balloon and the fourth balloon, via the introducing port, the syringe, the first supply port, the second supply port, the third balloon conduit and the fourth balloon conduit, the third and fourth balloons expand in the diameter direction, and when the piston moves inside the syringe toward the one end side in a state where the introducing valve is closed, the air inside the third balloon is moved into the fourth balloon via the third balloon conduit, the syringe, and the fourth balloon conduit, and thereby the third balloon contracts in the diameter direction and the fourth balloon expands in the diameter direction interlockingly with the contraction, thereby moving the one-side surface in parallel to the position close to the papilla with respect to the field of view direction of the objective lens by utilizing the expansion of the fourth balloon, while making the field of view direction of the objective lens and the protruding direction coincide with each other.

2. The endoscope system according to claim 1, wherein:
the second balloon is disposed, in the circumferential direction on the distal end side of the flexible tube portion, on a side close to the papilla along the field of view direction, and the first balloon is disposed on a side separate from the papilla, and when the second balloon contracts and the first balloon expands, the one-side surface is moved in parallel toward a side close to the papilla along the field of view direction to a position close to the papilla, to push up an upper side of the papilla by a distal end of the treatment instrument.

3. The endoscope system according to claim 1, wherein:
the third balloon is disposed, in the circumferential direction on the distal end side of the flexible tube portion, on one end side of a direction orthogonal to a field of view direction of the objective lens and the fourth balloon is disposed on the other end side of the direction orthogonal to the field of view direction of the objective lens, and when the third balloon expands and the fourth balloon contracts, or when the fourth balloon expands and the third balloon contracts, the one-side surface is moved in parallel in a direction orthogonal to the field of view direction to a position close to the papilla.

4. A side-view endoscope comprising:
an elongated insertion portion including:
 a bendable bending portion;
 a flexible tube portion having flexibility and provided on a proximal end side of the bendable bending portion; and
 a distal end portion provided on a distal end side of the bendable bending portion,
 wherein the elongated insertion portion is configured to be inserted into a lumen; and
four balloons disposed on a distal end side of the flexible tube portion, the balloons being expandable and contractable in a diameter direction of the elongated insertion portion in accordance with air feeding and air sucking by an air feeding/sucking device, and moving a one-side surface provided in the distal end portion in parallel to the diameter direction of the insertion portion, separately from bending of the bending portion, the one-side surface being located in a circumferential direction along an insertion direction of the elongated insertion portion and being parallel to a central axis of the elongated insertion portion, wherein the four balloons are disposed in the circumferential direction of the distal end side of the flexible tube portion and the four balloons include:
 a third balloon to which one end of a third balloon conduit is connected and a fourth balloon to which one end of a fourth balloon conduit is connected, the third and fourth balloons being provided opposed to each other at line-symmetric positions with respect to a first axis passing the central axis of the elongated insertion portion and parallel to a field of view direction of an objective lens provided on the one-sided surface: and
 a first balloon to which one end of a first balloon conduit is connected and a second balloon to which one end of a second balloon conduit is connected, the first and second balloons being provided opposed to each other at line-symmetric positions with respect to a second axis passing the central axis of the elongated insertion portion and orthogonal to the first axis, wherein an other end of the first balloon conduit and an other end of the fourth balloon conduit are connected to a first valve of a syringe, the syringe including an introducing port for introducing air from the air feeding/sucking device, an introducing valve for changing over whether or not to introduce the air from the air feeding/sucking device into the introducing port, a first supply port on one end side of the syringe and the first valve, a second supply port on the other end side of the syringe and a second valve, and a piston movable between the one end side and the other end side, and an other end of the second balloon conduit and an other end of the third balloon conduit are connected to the second valve of the syringe, wherein the balloons are configured such that, in a state where the field of view direction of the objective lens and the protruding direction of the treatment instrument protruded from an aperture formed on the one-side surface coincide with each other by fixing a bending angle of the bendable bending portion and in a state where an air supply direction is changed over to the first balloon conduit by the first valve, an air supply direction is changed over to the second balloon conduit by the second valve, the introducing valve is opened, and the piston is positioned in the syringe in the center between the one end side and the other end side of the syringe, when the air is supplied from the air feeding/sucking device to the first balloon and the second balloon via the introducing port, the syringe, the first supply port, the second supply port, the first balloon conduit, and the second balloon conduit, the first and second balloons expand in the diameter direction, and when the piston moves inside the syringe toward the one end side in a state where the introducing valve is closed, the air inside the second balloon is moved into the first balloon, via the second balloon conduit, the syringe, and the first balloon conduit, and thereby the second balloon contracts in the diameter direction and the first balloon expands in the diameter direction interlockingly with the contraction, thereby moving the one-side surface in parallel to a position close to a papilla with respect to the field of view direction of the objective lens by utilizing the expansion of the first balloon, while making the field of view direction of the objective lens and the protruding direction coincide with each other, and causing the field of view direction of the objective lens and the protruding direction of the treatment instrument protruded from the aperture formed on the one-side surface to coincide with each other before and after the movement of the one-side surface, and in a state where the field of view direction of the objective lens and the protruding direction of the treatment instrument protruded from the aperture formed on the one-side surface coincide with each other by fixing a bending angle of the bendable bending portion, and in a state where the air supply direction is changed over to the fourth balloon conduit by the first valve, the air supply direction is changed over to the third balloon conduit by the second valve, the introducing valve is opened, and the piston is positioned in the syringe in the center between the one end side and the other end side of the syringe, when the air is supplied from the air feeding/sucking device to the third balloon and the fourth balloon, via the introducing port, the syringe, the first supply port, and the second supply port, the third balloon conduit, and the fourth balloon conduit, the third and fourth balloons expand in the diameter direction, and when the piston moves inside the syringe toward the one end side in a state where the introducing valve is closed, the air inside the third balloon is moved into the fourth balloon via the third balloon conduit, the syringe, and the fourth balloon conduit, and thereby the third balloon contracts in the diameter direction and the fourth balloon expands in the diameter direction interlockingly with the contraction, thereby moving the one side surface in parallel to the position close to the papilla with respect to the field of view direction of the objective lens by utilizing the expansion of the fourth balloon, while making the field of view direction of the objective lens and the protruding direction coincide with each other, and causing the field of view direction of the objective lens and the protruding direction of the treatment instrument protruded from the aperture formed on the one-side surface to coincide with each other before and after the movement of the one-side surface.

\* \* \* \* \*